United States Patent
Xiao et al.

(10) Patent No.: US 6,771,732 B2
(45) Date of Patent: Aug. 3, 2004

(54) METHODS AND APPARATUS FOR FAST DIVERGENT BEAM TOMOGRAPHY

(75) Inventors: Shu Xiao, Sunnyvale, CA (US); Yoram Bresler, Urbana, IL (US); David C. Munson, Jr., Champaign, IL (US)

(73) Assignee: The Board of Trustees of the University of Illinois, Urbana, IL (US)

( * ) Notice: Subject to any disclaimer, the term of this patent is extended or adjusted under 35 U.S.C. 154(b) by 64 days.

(21) Appl. No.: 10/190,295

(22) Filed: Jul. 5, 2002

(65) Prior Publication Data

US 2003/0161443 A1 Aug. 28, 2003

Related U.S. Application Data

(60) Provisional application No. 60/360,390, filed on Feb. 28, 2002.

(51) Int. Cl.[7] ............................................. A61B 6/03
(52) U.S. Cl. ............................. 378/4; 378/15; 378/901
(58) Field of Search .............................. 378/4, 15, 901

(56) References Cited

U.S. PATENT DOCUMENTS

| | | | |
|---|---|---|---|
| 5,778,038 A | 7/1998 | Brandt et al. | 378/4 |
| 5,805,098 A | 9/1998 | McCorkle | 342/25 |
| 6,151,377 A | 11/2000 | Nilsson | 378/4 |
| 6,263,096 B1 * | 7/2001 | Boag et al. | 382/128 |
| 6,282,257 B1 * | 8/2001 | Basu et al. | 378/15 |
| 6,307,911 B1 * | 10/2001 | Basu et al. | 378/15 |
| 6,332,035 B1 * | 12/2001 | Basu et al. | 382/128 |
| 6,351,548 B1 * | 2/2002 | Basu et al. | 382/128 |

OTHER PUBLICATIONS

"Cone–Beam Reconstruction Using Filtered Backprojection"; Henrik Turbell; Institute of Technology, Linköpings Universitet; pp. 1–169; Feb. 2001.

"Fast Calculation of Multiple Line Integrals"; Brandt et al; SIAM J. Sci. Comput., vol. 20, No. 4, pp. 1417–1429; 1999.

Multi–Resolution Mixed Radix Quadtree SAR Image Focusing Algorithms; Oh et al; Third Annual Federated Laboratory Symposium on Advanced Sensors; pp. 139–143; Feb. 2–4, 1999.

"Iterative Techniques for Projection and Back–Projection"; Per–Erik Danielsson; Institute of Technology, Linköpings Universilet; pp. 1–39; Jun. 1997.

"Three–dimensional Reconstruction from Cone–beam Data in O($N^3$log $N$)Time"; Axelsson et al.; Phys. Med. Biol.; 39, pp. 477–491; 1994.

"A Fast Discrete Approximation Algorithm for the Radon Transform"; Martin Brady; SIAM J. Comput., vol. 27, No. 1, pp. 107–119; Feb. 1998.

(List continued on next page.)

*Primary Examiner*—David Bruce
(74) *Attorney, Agent, or Firm*—Greer, Burns & Crain, Ltd.

(57) ABSTRACT

A fast method for divergent-beam backprojection is proposed for generating an electronic image from a preprocessed divergent-beam sonogram, the sinogram being a collection of divergent beam projections. The method consists of the following steps: subdividing the sinogram into multiple sub-sinograms; performing a weighted backprojection of said sub-sinograms, to produce multiple corresponding sub-images; and aggregating said sub-images to create the electronic image. The subdivision of the sinogram into sub-sinograms can be performed in a recursive manner. A dual of the proposed method provides a fast means for reprojecting an electronic image, i.e., generating a divergent-beam sinogram from the image. These methods are applicable to fan-beam and cone-beam tomography utilizing a variety of scanning trajectories, including spiral. These methods do not require rebinning, and offer speedups similar to the FFT when compared to conventional backprojection and reprojection algorithms. Substantial computational savings are obtained without perceptible degradation or significant loss of numerical accuracy.

44 Claims, 35 Drawing Sheets

OTHER PUBLICATIONS

"Fast Feldkamp Reconstruction"; Turbell, et al,; Linköpings Universitel; Dec. 15, 1998.

"The PI–FAST Method for Approximate Helical Cone–beam Reconstruction"; Turbell et al.; Proc. Sixth Int. Meeting on Fully Three–Dimensional Image Reconstruction in Radiology and Nuclear Med.; Asilomar, Pacific Grove, CA; Oct. 30–Nov. 2, 2001.

"Multifrequential Algorithm for Fast 3D Reconstruction"; Rodet et al.; Proc. Sixth Int. Meeting on Fully Three–Dimensional Image Reconstr. In Radiology and Nuclear Med., Asilomar, Pacific Grove, CA; Oct. 30–Nov. 2, 2001.

"A Multilevel Domain Decomposition Algorithm for Fast $O(N^2 \log N)$ Reprojection of Tomographic Images"; Boag et al.; *IEEE Transactions on Image Processing*; vol. 9, No. 9; pp. 1573–1582; Sep. 2000.

"$O(N^2 \log_2 N)$ Filtered Backprojection Reconstruction Algorithm for Tomography";Basu et al.; *IEEE Transactions on Image Processing*: vol. 9, No. 10:pp. 1760–1773; Oct. 2000.

"Error Analysis and Perforamnce Optimization of Fast Hierarchical Backprojection Algorithms"; Basu et al; ; *IEEE Transactions on Image Processing*; vol. 10, No. 7; pp. 1103–1117; Jul. 2001.

"$O(N^3 \log N)$ Backprojection Algorithm for the 3–D Radon Transform"; Basu et al. .; *IEEE Transactions on Medical Imaging*; vol. 21, No. 2; pp. 76–88; Feb. 2002.

Seger et al.; "Real Time SAR Processing of Low Frequency Ultra Wide Band Radar Data"; European Conference on Synthetic Aperture Radar; Friedrichshafen, Germany; pp. 489–492; May 1998.

Hellsten et al; Synthetic–Aperture Radar Processing Using Fast Factorised Backprojection; European Conference on Synthetic Aperture Radar; Friedrichshafen, Germany; pp. 753–756; 2000.

\* cited by examiner-

Input: full set of modified (weighted and filtered) fan-beam projections
$G = \{g(p, kT), p = 0, \ldots P - 1, k = -K, \ldots K\}$,
image center $\bar{\delta}$, image size $N$, number of projections $P$ Parameters: $Q$ = number of exact decompositions;
$N_{min}$ = desired minimum subimage size.

Initialization: $\bar{\delta} = \bar{0}$.

FUNCTION FAN_FHBP(G,P,N,$\bar{\delta}$)
IF image size $N \leq N_{min}$
   FAN_FHBP = $f = B_{N,P}[\bar{\delta}]g$.
   RETURN
ENDIF
Partition the image into four same-sized subimages, $f_i, i = 1, \ldots 4$
   with centers at positions $\bar{\delta}_i = \bar{\delta} + \bar{\xi}_i$
$N \leftarrow N/2$
FOR $i = 1, 2, 3, 4$
   Truncate projections for subimage $i$: $G^{(1)} = \hat{\mathcal{K}}[\bar{\delta}_i]G$
   IF $Q < 1$ (approximate decomposition – reduce number of projections)
     FOR $p = 0, \ldots P - 1$
       Shift the truncated projections in $t$: $g^{(2)}(p, t) = \hat{\mathcal{M}}_+(p\Delta\theta, \bar{\delta}_i)g^{(1)}(p, t)$
     END FOR $p$
     Weight-Decimate in source angle: $G^{(3)} = W_2 \mathcal{D}_{\downarrow 2} W_1 G^{(2)}$
                                       $P' = P/2$
     FOR $p = 0, \ldots P' - 1$
       Shift back in $t$: $g'(p, t) = \hat{\mathcal{M}}_-(p\Delta\theta, \bar{\delta}_i)g^{(3)}(p, t)$
     END FOR $p$
   END IF
   $f_i = \mathcal{K}_N[\bar{\delta}_i]FAN\_FHBP(G', P', N, \bar{\delta}_i)$
END FOR $i$
$Q = Q - 1$
FAN_FHBP = $f = \sum_{i=1}^{4} f_i$
RETURN
END

METHODS AND APPARATUS FOR FAST DIVERGENT BEAM TOMOGRAPHY

This is a continuation of provisional patent application Serial No. 60/360,390, filed Feb. 28, 2002.

U.S. Pat. Nos. 6,263,096; 6,282,257; 6,307,911; 6,322,035; and 6,351,548 are incorporated by reference in their entirety.

The United States Government may have rights in this invention pursuant to one or more of the following: AFOSR/DARPA, No. F49620-98-1-0498: NSF, No. CCR-99-72980; and ARO/DARPA, No. DAAG55-98-1-0039.

FIELD OF THE INVENTION

This invention relates to methods and apparatus for divergent beam tomography, and more particularly to methods and apparatus for divergent beam tomography that reduce computational complexity without visually perceptible degradation or significant numerical inaccuracy.

BACKGROUND OF THE INVENTION

Tomographic reconstruction is a well-known technique underlying nearly all of the diagnostic imaging modalities, including x-ray computed tomography (CT), positron emission tomography (PET), single photon emission tomography (SPECT), and certain acquisition methods for magnetic resonance imaging (MRI). It is also widely used in manufacturing for nondestructive evaluation (NDE), and more recently for airport baggage inspection. The dominant data acquisition mode in current CT scanners is the fan-beam geometry, often combined with a helical or spiral scan.

In the interest of faster image acquisition, CT scanner technology is moving to cone-beam acquisition using area detectors. Already many of the CT scanners produced have a multirow detector (typically 16 rows), resulting in (low-angle) cone-beam acquisition. Area detectors for wide-angle cone-beam acquisition will be introduced in medical CT scanners over the next few years. Currently there is an unmet need for high-speed, 3D tomographic imaging for detection of concealed weapons and explosive devices. In other modalities, such as PET or SPECT, cone-beam acquisition is already the dominant format.

The reconstruction problem in fan-beam and in cone-beam CT is to recover a 2D or 3D image of an object from a set of its line-integral projections along lines diverging as a fan or a cone, respectively, from a source traveling on a specified acquisition trajectory or orbit. The fan-beam and cone-beam geometries are therefore instances of the divergent-beam geometry.

The method of choice for tomographic reconstruction is filtered backprojection (FBP) or convolution backprojection (CBP), both of which use a weighted backprojection step. This step is the computational bottleneck in the technique, with computational requirements scaling as $N^3$ for an N×N-pixel image in 2D, and at least as $N^4$ for an N×N×N-voxel image in 3D. Thus, doubling the image resolution from N to 2N results in roughly an 8-fold (or 16-fold, in 3D) increase in computation. While computers have become much faster, with the advent of new technologies capable of collecting ever larger quantities of data in real time (e.g., cardiac imaging with multi-row detectors, interventional imaging), and the move to 3D cone-beam geometry, there is still a growing need for fast reconstruction techniques. Fast reconstruction can speed up the image formation process, reduce the cost of a special-purpose image reconstruction computer (see below), or both.

The dual operation of backprojection is reprojection, which is the process of computing the projections of an electronically stored image. This process, too, plays a fundamental role in tomographic reconstruction. A combination of backprojection and reprojection can also be used to construct fast reconstruction algorithms for the long object problem in the helical cone-beam geometry, which is key to practical 3D imaging of human subjects. Furthermore, in various applications it is advantageous or even necessary to use iterative reconstruction algorithms, in which both back-projection and reprojection steps are performed several times for the reconstruction of a single image. Speeding up the backprojection and reprojection steps will determine the economic feasibility of such iterative methods.

In discussing fast methods, it is important to distinguish between the two main formats for tomographic data: (i) parallel-beam; and (ii) divergent-beam and its special cases. While the parallel-beam format is the most convenient for both theoretical and computational manipulations, divergent-beam is the format most commonly found in commercial medical and industrial CT scanners. Although originally a 2D method, fan-beam reconstruction is the key component in state-of-the-art methods for helical and multi-slice helical 3D (volumetric) reconstruction. New and future designs are expected to migrate to the cone-beam geometry. Thus, whether in 2D or 3D, the divergent-beam geometry is the dominant imaging format, and will most likely remain so for the foreseeable future.

In the limit of large source distance from the object, the divergent-beam geometry reduces to the parallel-beam geometry. Therefore, all data processing methods for the divergent-beam geometry (including the methods of this invention) are also applicable to the parallel-beam geometry. However, the converse is not true: for the small or moderate source distances found in practice, the two geometries are sufficiently different, that parallel-beam processing methods yield inferior or unsatisfactory results when applied directly to divergent-beam data. Thus, divergent-beam geometries require processing different from parallel-beam geometries.

The present invention addresses divergent-beam tomography. Some reconstruction methods rely on a process called rebinning, to rearrange (or interpolate) divergent-beam data into parallel-beam data, which is then processed by a parallel-beam algorithm. Other methods for 3D divergent-beam geometries rely on transforming the cone-beam data to 3D Radon transform data (or a derivative thereof). Instead, native divergent-beam methods (of which the present invention is a fast version) by definition process the divergent-beam data directly, without prior rebinning to parallel-beam data or transforming the data to the 3D Radon transform domain. The reconstruction process in native divergent-beam methods consists of preprocessing the projections (e.g., weighting and filtering), followed by a weighted divergent-beam backprojection operation and perhaps a divergent-beam reprojection operation, or a series of such operations. Such methods are therefore called divergent-beam filtered backprojection (DB-FBP) algorithms. Their computation is usually dominated by the backprojection and reprojection operations, just as for the parallel-beam case.

Divergent-beam reprojection can be performed by first performing a parallel-beam reprojection, and then rebinning the results, but here too, it is advantageous to use a native divergent-beam reprojection algorithm, which does not use rebinning.

The drawbacks of rebinning include possible artifacts and added computation, which limit the speedup. Rebinning also requires acquisition and manipulation of a large part of the data before processing can start, once again limiting speed. Methods that rely on a transformation to the 3D Radon domain have similar drawbacks. Thus, there is a need for methods and apparatus for divergent-beam tomography that overcome these drawbacks, that are highly flexible, and that provide large performance gains compared to methods that use conventional divergent-beam backprojection.

Special-purpose hardware has been the traditional avenue to speeding up the backprojection process. Special types of computers, using custom chips, or multiple processors, or combinations thereof, are designed to perform the necessary computations.

Drawbacks of this approach include the cost of multiple processors or custom hardware, and the fact that with the high rate of increase in the performance of general purpose computers, the special purpose architectures required quickly become obsolete. Thus, there is a need for fast processes for the divergent-beam geometry that do not require special-purpose hardware, and that are easily implemented on standard serial or parallel architectures, to make them more cost effective.

OBJECTS OF THE INVENTION

Accordingly, one object of this invention is to provide new and improved methods and apparatus for divergent-beam tomography.

Another object is to provide new and improved methods and apparatus for divergent-beam tomography that reduce computational complexity without visually perceptible degradation or significant numerical inaccuracy.

SUMMARY

In keeping with one aspect of this invention, a method is proposed for generating an electronic image from a preprocessed divergent-beam sinogram which is amenable to backprojection, the sinogram being a collection of divergent beam projections. The method can include the following steps: subdividing the sinogram into a plurality of sub-sinograms; performing a weighted backprojection of the sub-sinograms in the global coordinate system fixed to the object to produce a plurality of corresponding sub-images at proper locations in the global coordinate system; and aggregating the sub-images to create the electronic image. The subdivision of the sinogram into sub-sinograms can be performed in a recursive manner until each sub-sinogram represents a sub-image of a desired size, where the subdividing steps include a desired number of exact subdivisions and a desired number of approximate subdivisions.

In keeping with another aspect of this invention, a method is proposed for reprojecting an electronic image, that is, generating a divergent-beam sinogram from the image. The method can include the following steps: dividing the image into a plurality of sub-images; computing sub-sinograms of each sub-image in the global coordinate system; and aggregating the sub-sinograms to create the sinogram. The subdivision of the image can be performed in a recursive manner until each sub-image has a desired size, and the computation of sub-sinograms can be approximate in a desired number of levels in the recursion, and exact in the remaining levels of the recursion.

These methods offer speedups similar to the FFT when compared to conventional backprojection and reprojection algorithms. Substantial computational savings are obtained without perceptible degradation or significant loss of numerical accuracy.

BRIEF DESCRIPTION OF THE DRAWINGS

The above mentioned and other features of this invention and the manner of obtaining them will become more apparent, and the invention itself will be best understood by reference to the following description of an embodiment of the invention taken in conjunction with the accompanying drawings, in which:

FIG. 16 is pseudo-code for a fast fan-beam hierarchical backprojection;

DETAILED DESCRIPTION

Figure 1:
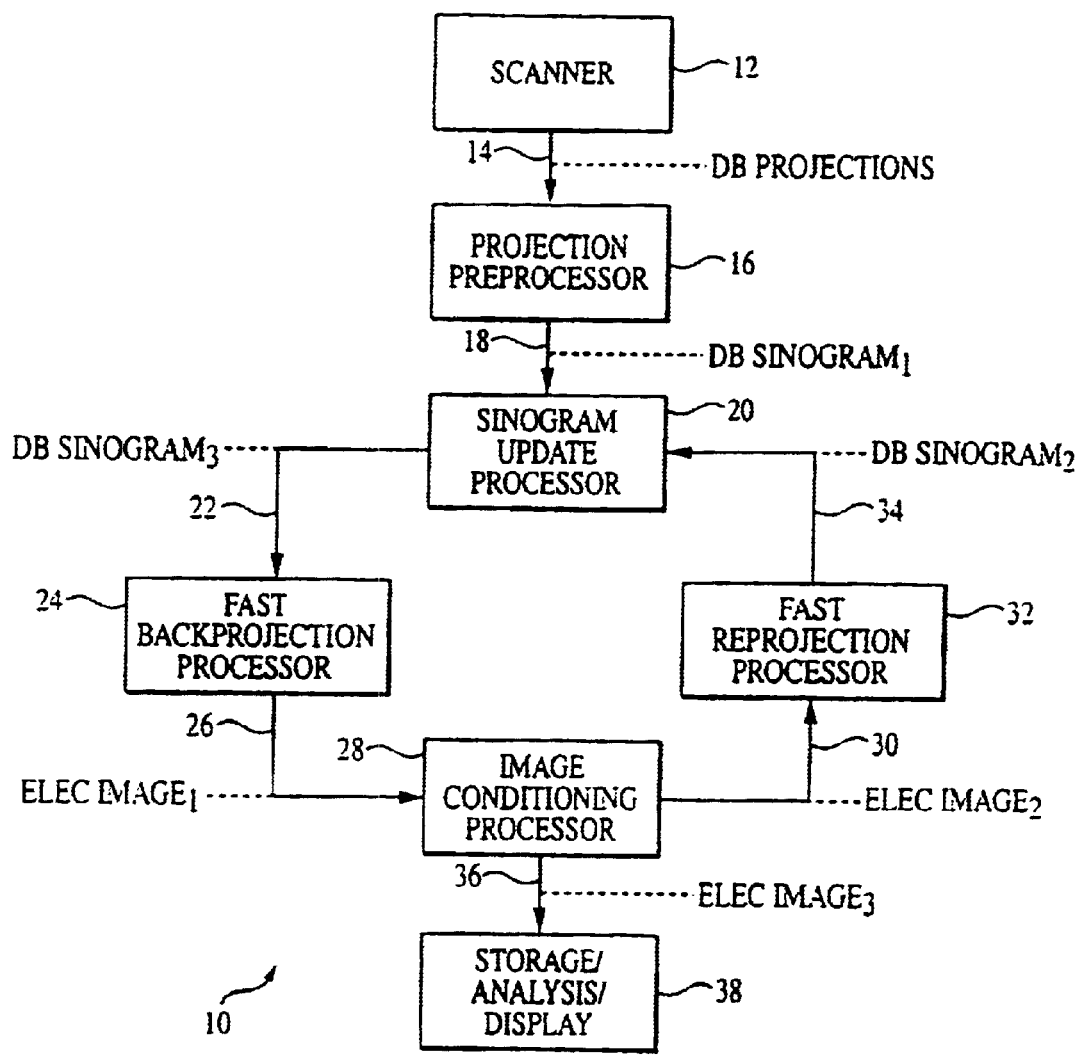
FIG. 1 is a block diagram of apparatus for use with the present invention.

The present invention has application in a variety of imaging apparatus, including CT scanners. Typical imaging apparatus 10 (FIG. 1) includes a scanner 12 which acquires data from an object such as a head, and sends raw data corresponding to divergent beam projections 14 to a projection pre-processor 16. The projection pre-processor 16 applies various conversions, normalizations, and corrections to the data, as well as weighting and filtering, which may be shift varying. The output of the projection pre-processor 16 is a divergent beam sinogram$_1$ 18, which is fed to a sinogram update processor 20. The sinogram update processor 20 possibly modifies the input sinogram$_1$ 18, using information from divergent beam sinogram$_2$ 34, for example correcting for various artifacts including beam-hardening, or as part of a multistep or iterative reconstruction procedure.

The output of the sinogram update processor 20 is a divergent beam sinogram$_3$ 22, which is input to a fast backprojection processor 24. The fast backprojection processor 24 is generally a computer or special purpose hardware, or any combination thereof, of any suitable type programmed to perform the exact and approximate backprojection algorithms described herein.

The output of the fast backprojection processor 24 is an electronic image$_1$ 26, which is input to an image conditioning processor 28. The image conditioning processor 28 performs necessary postprocessing of the electronic image, possibly including identification and extraction of artifact images, or images for further processing in a multi-step or iterative reconstruction process.

If desired, the image conditioning processor 28 can produce an electronic image$_2$ 30 that is fed to a fast reprojection processor 32. The fast reprojection processor 32 is generally a computer or special purpose hardware, or any combination thereof, of any suitable type programmed to perform the exact and approximate reprojection algorithms described herein. If desired, this processor can share the use of the same computer and hardware employed by the backprojection processor 24.

The output of the fast reprojection processor 32 is a divergent beam sinogram$_2$ 34, which is fed back into the sinogram update processor 20. The backprojection/reprojection process can continue until suitable results are obtained. While reprojection is not always needed, it is helpful in many situations.

When the electronic image$_1$ 26 is suitable, the image conditioning processor 28 produces an electronic image$_3$ 36, which is fed to a storage/analysis/display device 38. It is contemplated that the electronic image$_3$ 36 can be stored in a computer memory, and/or analyzed electronically for anomalies or dangerous materials, for example, and/or displayed, and/or printed in some viewable form.

The fast divergent-beam backprojection algorithms of this invention build upon the fast hierarchical backprojection algorithm (FHBP) for parallel-beam tomography described in U.S. Pat. No. 6,287,257. Likewise, the fast divergent-beam reprojection algorithms of this invention build upon the fast hierarchical reprojection algorithms (FHRP) for parallel-beam tomography described in U.S. Pat. Nos. 6,263,096 and 6,351,548. Backprojection and reprojection are closely related and their fast algorithms derive from the same principles. The more commonly used fast backprojection will be described in greater detail.

To understand the parallel-beam FHBP algorithm, consider an N×N image with an attached global coordinate system, with the origin at the center of the image. Consider decomposing this large N×N image into four smaller images, called subimages, of size N/2×N/2, each located in a different quadrant of the global coordinate system. Two properties of the Radon transform are used in the derivation of the FHBP algorithm. (i) The bow-tie property says that for a half-sized image centered at the origin of the global coordinate system, the spectral support of the projections with respect to the angular variable is also decreased by half. This implies that a centered half-sized image can be reconstructed from a sinogram comprising half the number of projections. (ii) The shift property says that the parallel projections of a shifted image correspond to shifted parallel projections of the original image.

Suppose now that a sinogram comprising P filtered projections is available to reconstruct the entire image f. To reconstruct one of the subimages $f_i$, the P projections are first truncated to the support of the projection of the subimage, then shifted to correspond to a centered version of the subimage, and finally decimated to P/2 projections with respect to the angular direction. The centered version of subimage $f_i$ is then reconstructed from these new P/2 projections, and the subimage shifted back to its correct location in the global coordinate system. This is performed for each of the four subimages, which, when aggregated together provide a reconstruction of the entire image f. A total of $4c(P/2)(N/2)^2 = cP\,N^2/2$ operations are necessary to reconstruct four subimages, where c is a constant. This reduces the original reconstruction cost by one-half. Applying the decomposition recursively to decrease the image size by one-half at each step, permitting formation of half-sized subimages using one-half the number of projections, the total computational cost can be reduced to $O(N^2 \log N)$.

The dual of this decomposition and aggregation approach is used in the fast hierarchal parallel-beam reprojection algorithm, the FHRP, described in U.S. Pat. Nos. 6,263,096 and 6,351,548.

The present invention for divergent-beam backprojection and reprojection is based on the idea of hierarchically decomposing the image, and then reconstructing (or reprojecting) subimages using a divergent-beam subsinogram comprising fewer divergent-beam projections. An immediate difficulty that arises, however, when trying to apply the ideas of the parallel beam FHBP or FHRP to the divergent-beam scenario, is that the shift property (ii), above, no longer applies. That is, the divergent-beam projections of a shifted subimage do not correspond to shifted divergent-beam projections of the original subimage. Because the parallel beam FHBP and FHRP use this property, the parallel-beam approach must be modified for the divergent-beam scenario.

The algorithms of the present invention use a different procedure for the decomposition, which does not involve shifting of the subimages relative to the center of the global coordinate system, which is fixed to the object, that is, to the full-size image. Like the parallel-beam FHBP, the new divergent-beam backprojection algorithms have two types of decompositions, one exact but slow, the other approximate, but fast. The exact divergent-beam decomposition of the new algorithms does not have to involve any data shifting at all; it only involves truncation of the sinogram to subsinograms that correspond to the subimages. These subsinograms are then backprojected in the global coordinate system, producing the corresponding subimages at the correct locations in the global coordinate system. The approximate divergent-beam decomposition uses a procedure different from the one used in the parallel-beam FHBP to reduce the number of projections used to reconstruct a subimage of a smaller size. This new procedure involves truncation and shifting only of the projections, but not of the subimages. This new procedure might also include weighting, which was not used in the FHBP. Analogous statements apply to the new procedure for divergent-beam reprojection.

To reconstruct a subimage of half the size, appropriately truncated (weighted and filtered) divergent-beam projections are shifted by a distance determined by the position of the projection of the center of the subimage in the global coordinate system, and then decimated by two in the source position parameter, and shifted back by the same amount. The subimage can then be reconstructed, to a good approximation, from this reduced set of projections. For both exact and approximate weighted backprojection onto a subimage, all calculations involving image coordinates, including the weighting, are done in the absolute or global image coordinates, referred to the origin of the full-sized image. Combining the exact and approximate decompositions in a recursive form leads to fast hierarchical backprojection algorithms for divergent beam geometries. Like their parallel-beam FHBP counterparts, these algorithms offer a tradeoff between computation and accuracy by selecting the number of exact versus approximate decompositions, and by adjusting various algorithm parameters.

Divergent-Beam Imaging Geometries

The general divergent-beam acquisition geometry for 3D tomography involves a vertex (usually a source) of divergent rays moving on a trajectory in 3D space around the imaged object, and a detector surface, on which line integrals along the source rays through the imaged object are measured. Other imaging modalities, having convergent rather than divergent beam geometries, such as those arising in emission tomography (SPECT and PET), can be transformed to this geometry.

The acquisition geometry is usually classified by the shape of the detector and associated ray sampling scheme, and by the source trajectory or orbit. The two most common classes of detectors are (i) planar detector surface with equispaced detectors; and (ii) cylindrical detector surface with rays sampled equispaced in azimuth angle, and linearly-equispaced in height. In 3D imaging with a surface detector, divergent-beam geometries are also known as cone-beam geometries.

In a special case of divergent-beam 2D acquisition, the detector surface is reduced to a single line or an arc of detectors, giving rise to so-called colinear equispaced, and equiangular fan-beam geometries, respectively. These fan-beam geometries are widely deployed in current commercial systems.

Of the various source orbits that have been proposed, the most common are the single circular orbit, and the helical (or spiral) orbit. However, other orbits, such as two circles, or a circle and a line are also of practical interest, and arbitrarily perturbed versions of these various orbits also occur in practice.

The process, algorithms, and apparatus of this invention are applicable to the general divergent-beam geometry, and can be specialized to any of the particular geometries mentioned earlier or to other instances of divergent-beam geometry. Likewise, the methods of this invention are applicable to any mathematically equivalent data set, including, but not limited to, convergent beam geometries. For illustrative purposes, the methods will be explained in some detail for the following cases:

1. Single circular source orbit
    (a) colinear equispaced fan-beam geometry
    (b) equiangular fan-beam geometry
    (c) planar cone-beam geometry.
2. General cone-beam geometry with planar detector
3. Helical source orbit How the general process is specialized to these cases will be demonstrated, from which it will be apparent that the algorithm for one detector shape and source orbit is easily modified for a different detector shape and source orbit.

Divergent-Beam Imaging Geometries With Arbitrary Orbit

Figure 2:
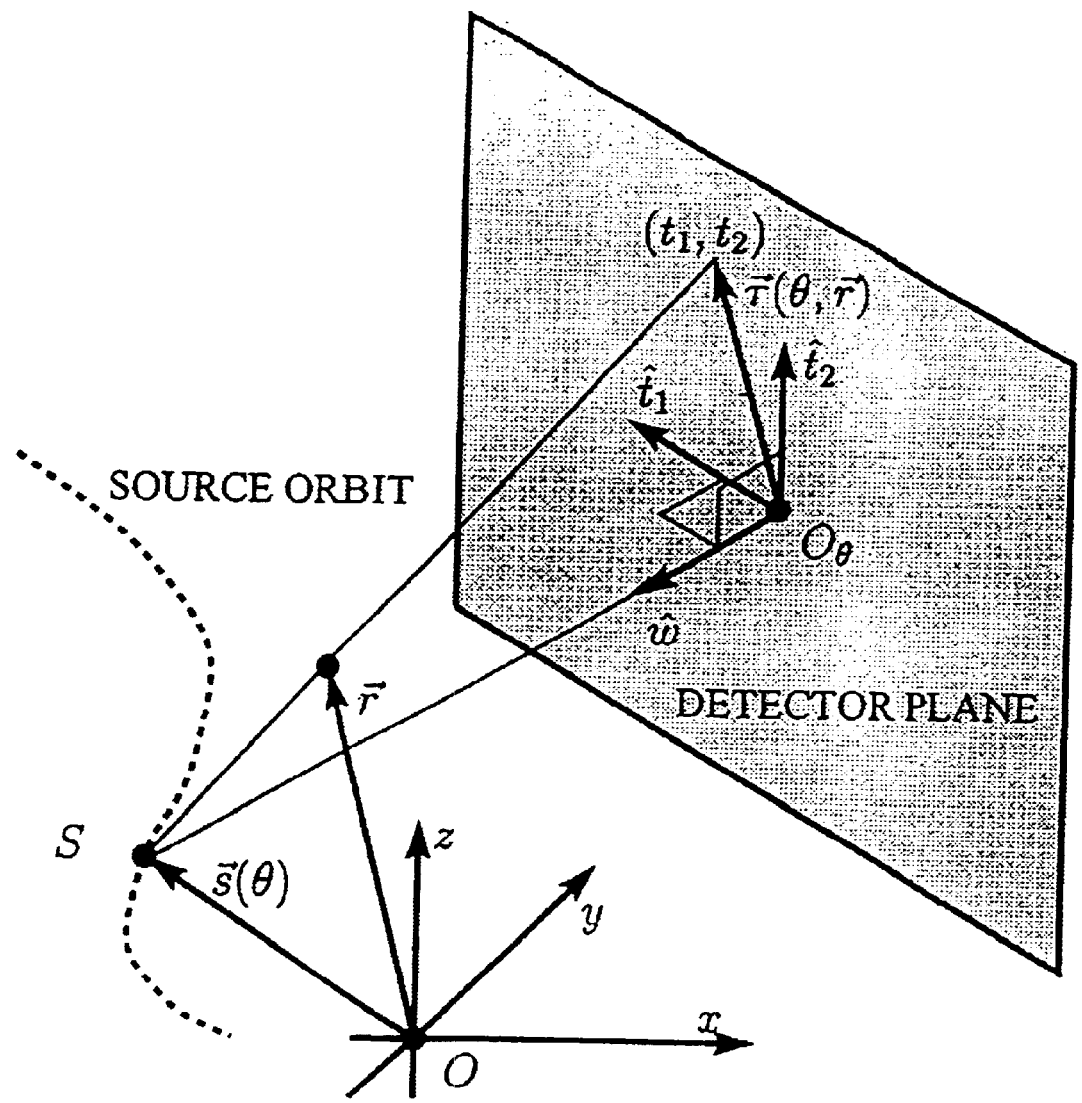
FIG. 2 is a diagram of a planar equispaced cone-beam geometry.

The planar equispaced cone-beam geometry where the detectors are evenly spaced on a planar surface is illustrated in FIG. 2. In this case, the detector plane is allowed to have an arbitrary position and orientation for each source position.

The source S of divergent rays travels on an orbit around the 3D object, defined by the source position vector $\vec{s}(\theta)=[x(\theta),y(\theta),z(\theta)]^T$ relative to the center O of a global coordinate system fixed to the object, with the source location on its orbit specified by the parameter $\theta$, with $\theta_{min} \leq \theta \leq \theta_{max}$. For each $\theta$, a 3D coordinate system attached to the detector is defined, so that the origin $O_\theta$ is the orthogonal projection of the orbit point $\vec{s}(\theta)$ onto the detector plane. Orthonormal vectors $\hat{t}_1$ and $\hat{t}_2$ are chosen within the detector plane, whereas $\hat{w}$ is the unit vector orthogonal to the detector plane, pointing from $O_\theta$ to the source. A point $\vec{t} = t_1 \hat{t}_1 + t_2 \hat{t}_2$ in the detector plane is defined in terms of its coordinates $(t_1, t_2)$. In this system the source orbit point is expressed as $D(\theta)\hat{w}$, where $D(\theta)$ is the distance between the source and the detector. (In SPECT, $D(\theta)$ is the focal length of the cone-beam collimator.)

Let $\vec{r} = [x,y,z]^T$ denote position in the 3D image (i.e., object), and let $\vec{\tau}(\theta, \vec{r}) = [\tau_1(\theta, \vec{r}), \tau(\theta, \vec{r})]^T$ denote the $t_1, t_2$ position of the intersection with the detector plane of the source ray passing through point $\vec{r}$ (see FIG. 2). The divergent-beam projection $(Pf)(\theta, t_1, t_2)$ of the object f at source orbit position $\theta$ and detector position $(t_1, t_2)$ is the line integral along the source ray parameterized by $(\theta, t_1, t_2)$, and is given by $$(Pf)(\theta,t_1,t_2) = \int_{\vec{r} \in pullout; zu192400.9003} f(\vec{r}) \delta[(t_1,t_2) - \vec{\tau}(\theta, \vec{r})] d\vec{r} \quad (1)$$

where $\delta(\vec{r})$ is the Dirac delta function. The same acquisition geometry can be used to describe a situation wherein the source rays converge toward the source rather than diverge from it. Therefore, the processes of this invention are equally applicable to convergent beam geometries.

Projections are acquired at P discrete source positions defined by a parameter along the source orbit, $\theta_p=p\Delta\theta, p=0, \ldots P-1$, usually but not necessarily with uniform spacing $\Delta\theta=(\theta_{max}-\theta_{min})/P$. The term $(Pf)(\theta_p,\bullet)$ (for all values of $\vec{t}$) is called a divergent-beam projection at source position $\theta_p$. The detector plane is usually sampled on a uniform rectangular grid, with possibly different intervals $T_1$ and $T_2$ on the $t_1$ and $t_2$ axes.

A collection of divergent-beam projections at different source positions will be called a divergent-bean sinogram. The same term will also be used for a set of preprocessed divergent-beam projections, or any other mathematically equivalent data set. The collection of projections in a sinogram may be incomplete, comprising as few as a single projection.

Some special cases of the general divergent-beam geometry will now be described.

Cone-Beam Helical Tomography With Planar Detector

Figure 3:
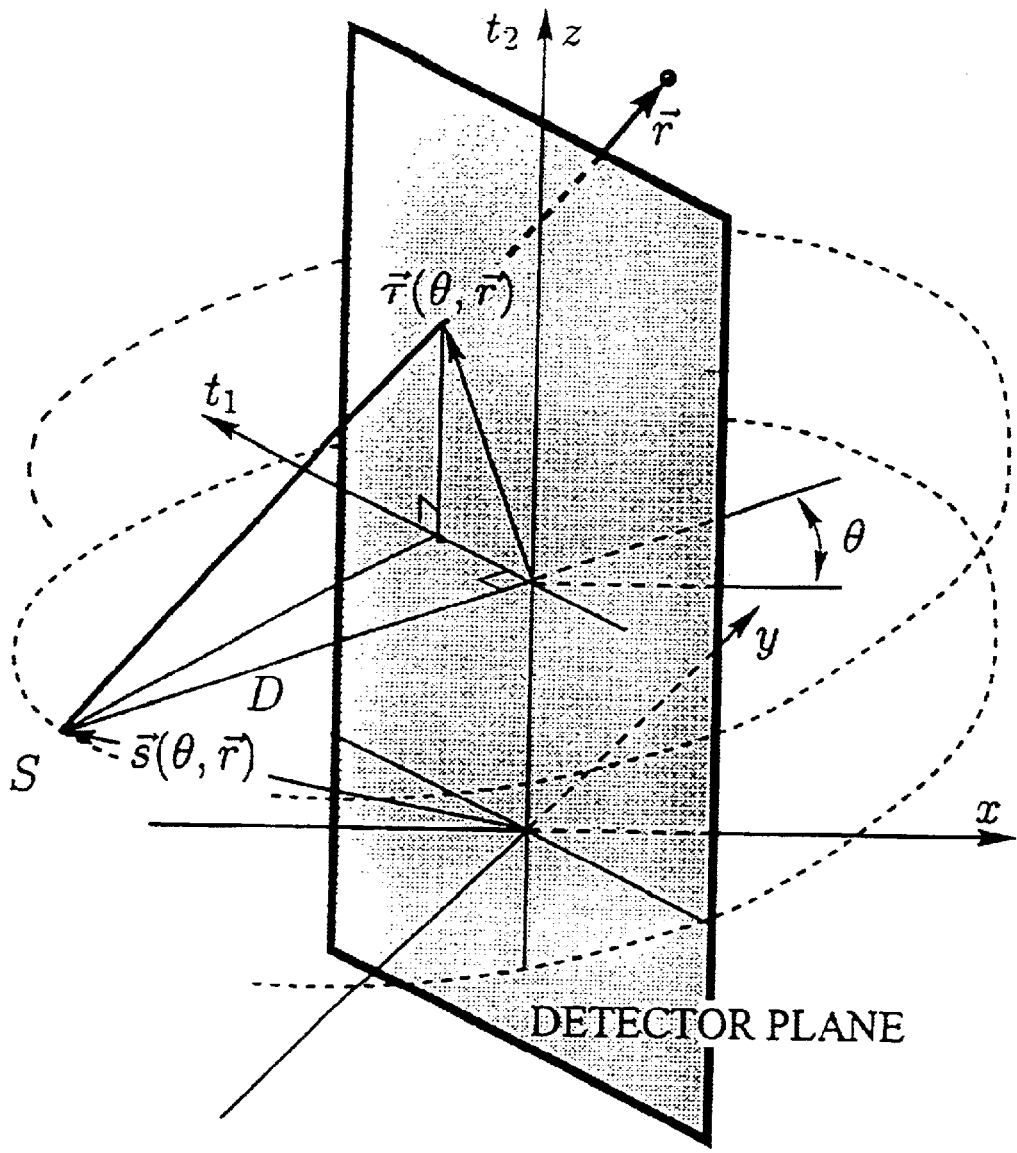
FIG. 3 is a diagram of a planar equispaced helical cone-beam geometry.

The source orbit in this case is a helix or spiral around the axis, as shown in FIG. 3, defined by $\vec{s}(\theta)=[D\cos(\theta), D\sin(\theta), h\theta/2\pi]$, where the radius D is constant, and h is known as the pitch of the helix.

Parameter $\theta$ in this case indicates the source angle in the (x,y) plane, relative to the x axis. The detector plane is assumed without loss of generality to contain the z axis, and to rotate with the source motion, so that it is perpendicular to the projection of the source vector $\vec{s}$ onto the (x,y) plane for each $\theta$. The origin $O_\theta$ in the detector plane falls on the z axis in this case. The $t_2$ axis coincides with the z axis, and the $t_1$ axis is parallel to the (x,y) plane. (Other common choices, e.g., where $\hat{t}_1$ is parallel to the tangent of the orbit at position $\theta$, and $\hat{t}_2$ is orthonormal to it, can be reduced to the case described herein by a coordinate rotation.)

Although, in practice, the detector plane may be located differently, simple linear coordinate transformation will convert projections acquired on the actual detector plane to projections acquired on the virtual detector assumed above, with uniform spacing along the $(t_1, t_2)$ coordinates.

Cone-Beam Imaging With a Single Circular Orbit and Planar Detector

Figure 4:
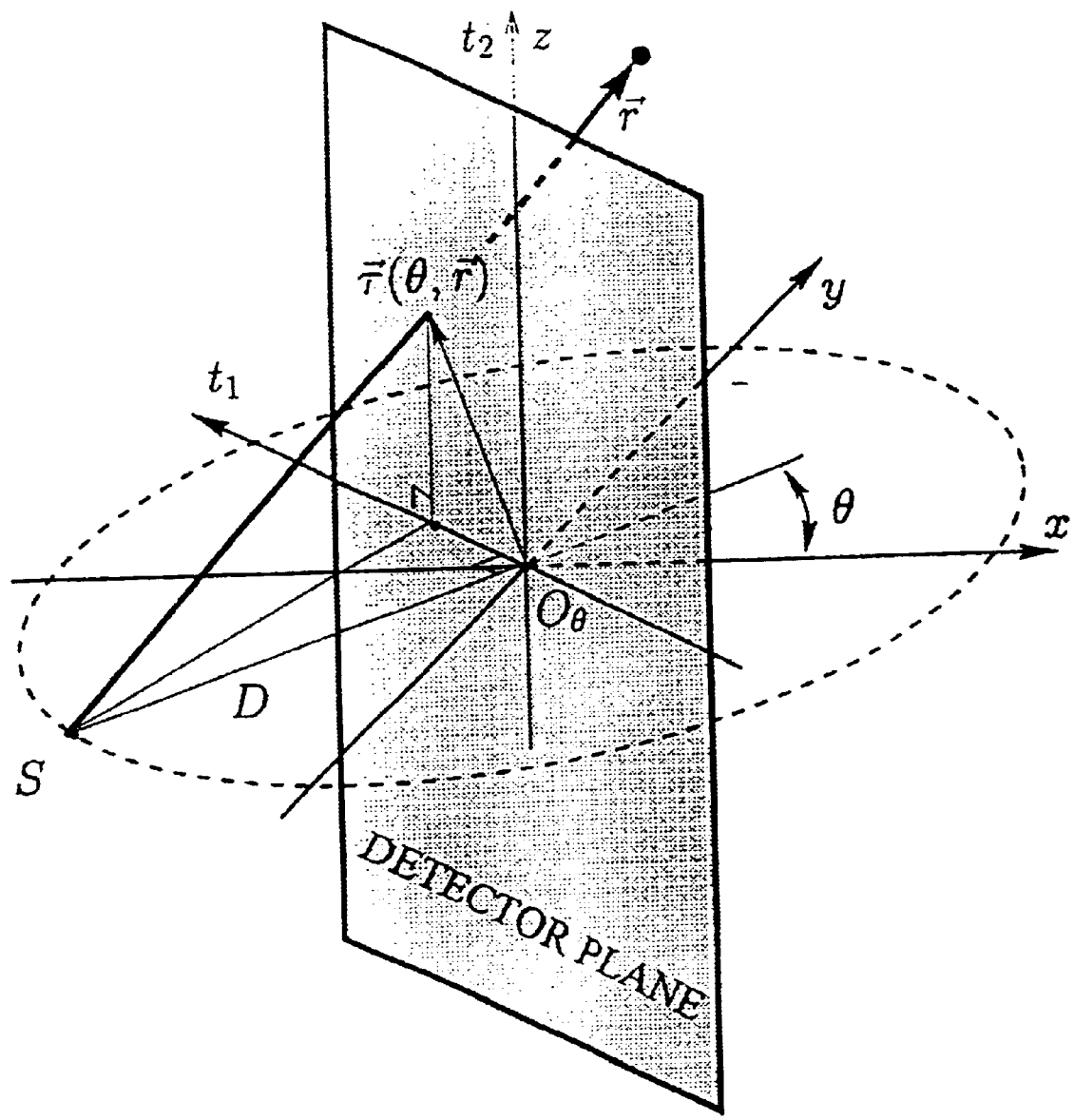
FIG. 4 is a diagram illustrating a cone-beam tomography with a circular source orbit and a planar equispaced detector.

The source orbit in this case, illustrated in FIG. 4, is a special case of the helical orbit, with zero pitch, h=0, i.e., it lies on a single circle $\vec{s}(\theta)=[D\cos(\theta), D\sin(\theta), 0]$ of radius D entered at the origin O, in the x,y plane. The detector plane is assumed, without loss of generality, to contain the z axis, and be perpendicular to the source-to-center line $\overline{SO}$.

Consider a point $\vec{r}=[x,y,z]^T$ in the object. The position $\vec{\tau}(\theta, \vec{r})$ of its cone-beam projection onto the detector, for detector angle $\theta$, is given by $$\tau_1(\theta, \vec{r}) = \frac{D(y\cos\theta - x\sin\theta)}{D + x\cos\theta + y\sin\theta} \quad (2)$$

$$\tau_2(\theta, \vec{r}) = \frac{Dz}{D + x\cos\theta + y\sin\theta} \quad (3)$$

These explicit expressions will be useful later in the explanation of the fast algorithms.

Fan-Beam Tomography with a Circular Orbit and Colinear Equispaced Detector

Figure 5:
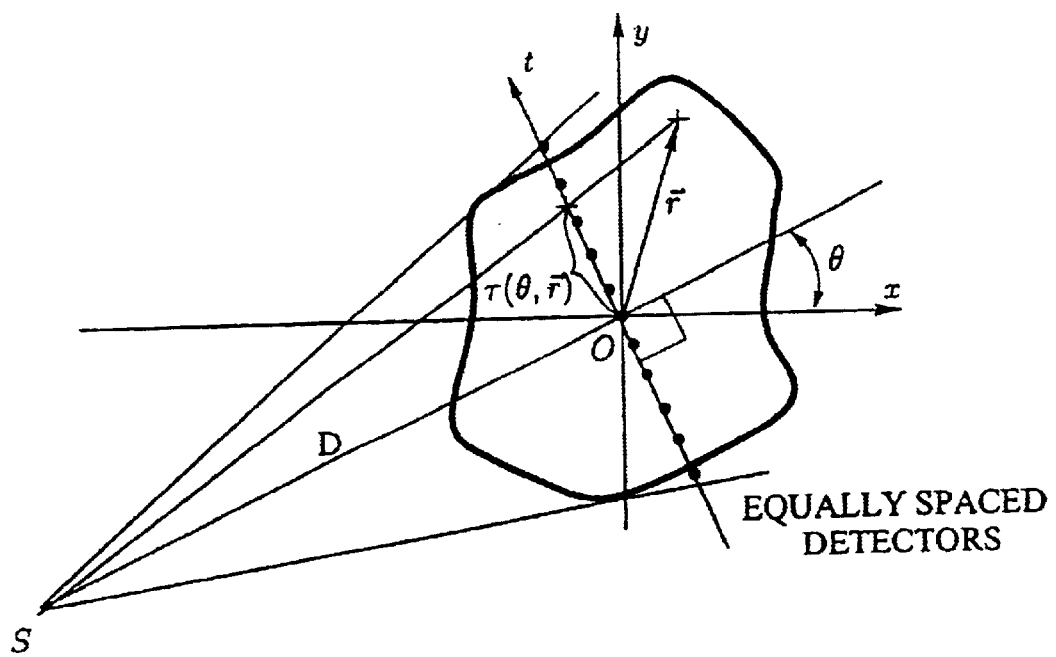
FIG. 5 is a diagram of colinear equispaced fan-beam geometry.

In this case, illustrated in FIG. 5, a single cross-section of the object is imaged, and a 2D image is reconstructed. The source orbit is again a circle of radius D in the (x,y) plane, centered at the origin O, with the source position indicated by the source angle $\theta$. The detector, however, is restricted to a single line (the t axis) in the (x,y) plane, and is assumed, without loss of generality, to pass through the center of rotation O of the source, and be perpendicular to the source-to-center line $\overline{SO}$. The detector elements are evenly spaced on the t axis.

Let $\vec{r}=[x,y]^T$ denote position in the 2D image, and let $\tau(\theta, \vec{r})$ denote the t position of the intersection with the t-axis of the source ray passing through point $\vec{r}$ (see FIG. 5). The fan-beam projection $(Pf)(\theta, t)$ of the object f at source angle $\theta$ and detector position t is the line integral along the source ray parameterized by $(\theta, t)$, and is given by $$(Pf)(\theta, t) = \int_{\vec{r}\in pullout; zu192400.9002} f(\vec{r}) \delta[t - \tau(\theta, \vec{r})] d\vec{r} \quad (4)$$

Projections are acquired at P discrete source angles $\theta_p = p\Delta\theta$, $p=0, \ldots P-1$ with uniform spacing $\Delta\theta = \theta_{max}/P$. The term $(Pf)(\theta_p,\bullet)$ (for all values of t) is a projection at source angle $\theta_p$, and a collection of projections for different p is a sinogram. The maximum source angle $\theta_{max}$ is equal to $2\pi$ in the case of a full scan, but can take other values in the case of a short scan or an over-scan. Partial data sets can comprise projections at any subset of angles.

In each case of divergent-beam geometry a curved, rather than planar, detector surface may be used, often with a modified ray sampling scheme. For example, for helical or single circular orbit cone-beam imaging, the detector surface is often chosen to lie on the surface of a cylinder centered on the source, and the ray sampling is equiangular in azimuth, and equispaced in height z. This is illustrated for the single circular source orbit in FIG. 6, where the curved detector is chosen to contain the z axis.

Figure 7:
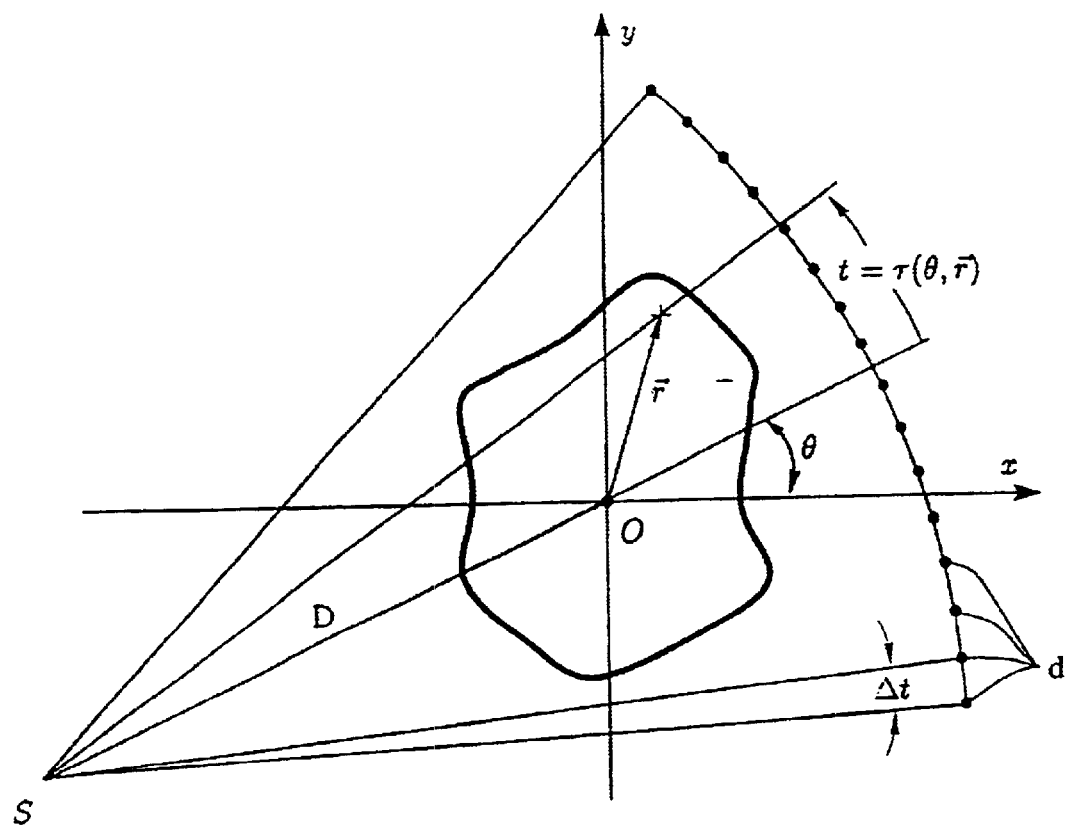
FIG. 7 is a diagram of an equiangular fan-beam geometry.

The relationship between the cylindrical and planar detector shapes in general is captured by studying the fan-beam geometry. In the fan-beam geometry with equiangular ray sampling, shown in FIG. 7, the detectors d are equispaced in angles, with spacing $\Delta t$, on an arc centered on the source S. Thus, in this imaging geometry, fan angle t replaces the detector position t appearing in the colinear equispaced fan-beam geometry. Let $\tau(\theta, \vec{r})$ now denote the fan angle position of the ray passing through point $\vec{r}$, as shown in FIG. 7. The projections are then again given by formula (4).

It is contemplated that there are other instances of fan-beam geometry which are likewise special cases of divergent-beam geometry, to which this invention is applicable.

Divergent-Beam Filtered-Backprojection Reconstruction and Reprojection

Native (direct) inversion of divergent-beam data, whether approximate, or exact, can be formulated as a weighted filtered backprojection. First, the divergent-beam sinogram is preprocessed, for example, the projections comprising the sinogram are weighted and filtered producing the modified divergent-beam sinogram comprising projections $g(p, \vec{t})$ corresponding to source positions $\theta_p$. The filtering may be simple shift-invariant ramp filtering as in the case of fan-beam or approximate cone-beam reconstruction, or much more involved shift varying filtering, as in the case of exact cone-beam reconstruction. The weighting and filtering may be even more general, producing two or more projection sets, whose contributions have to be summed, as in the case of exact or quasi-exact methods for reconstruction from helical cone-beam data with a partially-scanned long object. For the sake of brevity and generality, the data to be backprojected, whatever the preprocessing used to obtain it from original divergent-beam projection data, will be referred to as "divergent-beam projection data," or "divergent-beam sinogram". For fixed p it will be referred to as a "divergent-beam projection" (at source position $\theta_p$), and denoted by function $g(p,\cdot)$.

The 3D image is then reconstructed by the conventional divergent-beam discrete-$\theta$ backprojection $$f(\vec{r}) = \sum_{p=0}^{P-1} W(p\Delta\theta, \vec{r})g[p, \vec{\tau}(p\Delta\theta, \vec{r})]\Delta\theta, \qquad (5)$$

where $W(\theta, \vec{r})$ is an appropriate weight function. This discrete backprojection formula approximates the integral expression for the backprojection that uses projections measured for all $\theta$. In practice, $g(p, \vec{t})$ is also sampled in $\vec{t}$, because of the use of discrete detectors. This requires interpolation of $g$ in the variable $\vec{t}$ to implement the backprojection, because $\vec{\tau}(p\Delta\theta, \vec{r})$ does not usually correspond to an available sample position. The backprojection formula for the 2D fan-beam case has identical form, except that $\tau$ is scalar, and $\vec{r}$ two-dimensional.

The computational cost of 3D cone-beam backprojection for an N×N×N image is $cN^3P$, where the constant $c$ depends on implementation details such as complexity of the interpolation. In contrast, the computational cost of weighting and ramp filtering is only $O(PN^2 \log N)$ when the filtering is shift-invariant, and the convolution is performed using FFT's. Even more elaborate forms of filtering can often be performed at similar cost. Therefore, the cost of backprojection dominates the cost of conventional cone-beam reconstruction, which has cost $O(PN^3)$, or $O(N^4)$, when, as is often the case, $P=O(N)$. The situation is similar in 2D fan-beam reconstruction, where the complexities of the filtering and backprojection steps are $O(N^2 \log N)$ and $O(N^3)$, respectively.

Native (direct) divergent-beam reprojection of an electronically stored image f is an implementation of equation (1). In practice, f is only available in discrete form, and only samples in $\vec{t}$ of $(Pf)(\theta_p, \vec{t})$ are computed. For example, f may be represented by a series $$f(\vec{r}) = \sum_{i,j,k=1}^{N} \beta_{ijk} \phi_{ijk}(\vec{r}), \qquad (6)$$

where the coefficients $\beta_{ijk}$ are the discrete representation of f, and $\phi_{ijk}(\vec{r})$ are localized basis functions such as a tensor product of splines or the standard pixel basis function, i.e., the indicator function on the ijk-th voxel, as described e.g., in U.S. Pat. Nos. 6,263,096 and 6,287,257 for 2D, and in U.S. Pat. No. 6,332,035 for 3D. The projection can then be computed by $$(Pf)(\theta_p, \vec{t}) = \sum_{i,j,k=1}^{N} \beta_{ijk} \phi_{ijk}(\theta_p, \vec{t}), \qquad (7)$$

where $\phi_{ijk}(\theta_p, \vec{t}) = (P\phi_{ijk})(\theta_p, \vec{t})$ is the divergent-beam projection of basis function $\phi_{ijk}(\vec{r})$, as defined by equation (1). These projections of the basis functions can usually be computed using an analytical expression, or stored in a lookup table. As with backprojection, the cost of native reprojection is $O(N^4)$ in 3D, or $O(N^3)$ in 2D.

In the case of a curved detector, where $t_1,t_2$ are appropriate coordinates on the detector, let $\vec{\tau}(\theta, \vec{r})$ now denote the $(t_1,t_2)$ position on the detector plane of the source ray passing through point $\vec{r}$. The projections, which are again given by formula (1), can be computed using equation (7), with $\phi_{ijk}(\theta_p, \vec{t}) = (P\phi_{ijk})(\theta_p, \vec{t})$ denoting the divergent-beam projection of basis function $\phi_{ijk}(\vec{r})$ on the curved detector. Likewise, the reconstruction can again be expressed as a weighted backprojection of appropriately modified projections $g(p, \vec{t})$, where $t_1,t_2$ are appropriate coordinates on the curved detector. The backprojection is given by the same formula (5) as before, but with a different weighting function $W(\theta, \vec{r})$. For example, in the 2D equiangular fan-beam geometry, the fan angle t replaces the displacement t on the line detector of the equispaced colinear geometry. The considerations stemming from the discreteness of $\vec{t}$ are the same as those in the planar detector algorithms, as are the computational complexity considerations.

As already discussed, whether in 2D or 3D, the backprojection step (and reprojection, if used) is usually the most expensive computationally, and it is therefore the target of the present invention. A novel general process of fast backprojection applicable to all divergent-beam geometries will be described. To simplify the explanation, though, fast backprojection and reprojection will first be described for the 2D fan-beam geometries.

Figure 8:
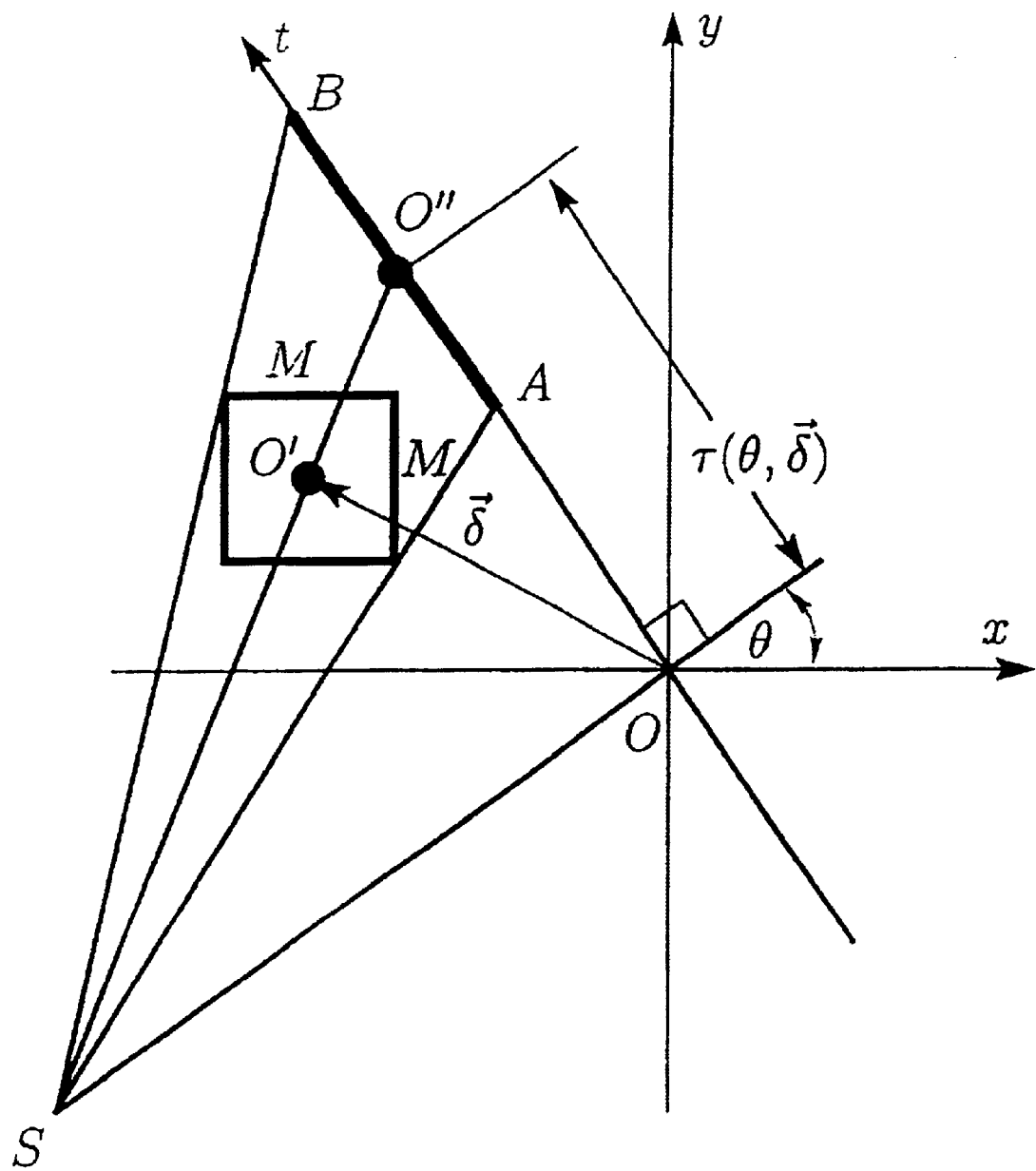
FIG. 8 is a diagram of collinear equispaced fan-beam projection geometry for an M×M subimage.

Fast Native Backprojection and Reprojection Algorithms for Colinear Equispaced Fanbeam Geometry Consider the backprojection operation for a sub-image $f'(\vec{r})$ of f, shown in FIG. 8. Let $K_M[\vec{\delta}]$ be an image truncation operator defined by $$\mathcal{K}_M[\vec{\delta}]f(\vec{r}) = \begin{cases} f(\vec{r}) & \text{if } \|\vec{r} - \vec{\delta}\|_\infty \leq M/2 \\ 0 & \text{else} \end{cases}, \qquad (8)$$

where $\|\vec{r}\|_\infty = \max\{x,y\}$. Thus $f' = K_M[\vec{\delta}]f$ is a sub-image of f, of size M×M centered at $O' = \vec{\delta} \in_R^2$. The backprojection in the global coordinate system onto subimage f' (located in its correct position in the global coordinate system) using Q projections at source angles $p\Delta\theta, p=0 \ldots Q-1$ is given by $$f'(\vec{r}) = \mathcal{B}_{M,Q}[\vec{\delta}]g(\vec{r}) = \mathcal{K}_M[\vec{\delta}]\sum_{p=0}^{Q-1} W(p\Delta\theta, \vec{r})g[p, \tau(p\Delta\theta, \vec{r})]\Delta\theta, \qquad (9)$$

$$\Delta\theta = \theta_{\max}/Q.$$

The term $B_{M,Q}[\vec{\delta}]$ denotes the associated backprojection operator. Thus, in particular, $f = B_{N,P}[\vec{0}]g$.

Because of the locality of the backprojection, only part of the projection $g(p,\cdot)$ contributes to the backprojection onto f'. This part is denoted by $\hat{K}_M[\vec{\delta}]g$, where $\hat{K}_M[\vec{\delta}]$ is the operator that, for each $\theta_p$, truncates $g(p,t)$ in the variable t to the support $\Xi = \overline{AB}$ of the projection of the support of the subimage $f' = K_M[\vec{\delta}]f$ (see FIG. 8). The truncation intervals determining $\hat{K}_M[\vec{\delta}]$ can be precomputed for all source angles $\theta_p$, and subimage sizes M and locations $\vec{\delta}$ of interest. Alternatively, a simpler conservative approximation can be used, at somewhat increased computational cost in the hierarchical algorithm owing to overestimation of the necessary support of projections requiring shifting and decimation.

It follows from the localization of backprojection that if $f = B_{N,P}[\vec{0}]g$ then $$f' = \mathcal{K}_M[\vec{\delta}]f = B_{M,P}[\vec{\delta}]\hat{\mathcal{K}}_M[\vec{\delta}]g, \tag{10}$$

that is, the backprojection onto f' can be obtained by a backprojection of size (M,P) of the appropriately truncated projections.

Figure 9:
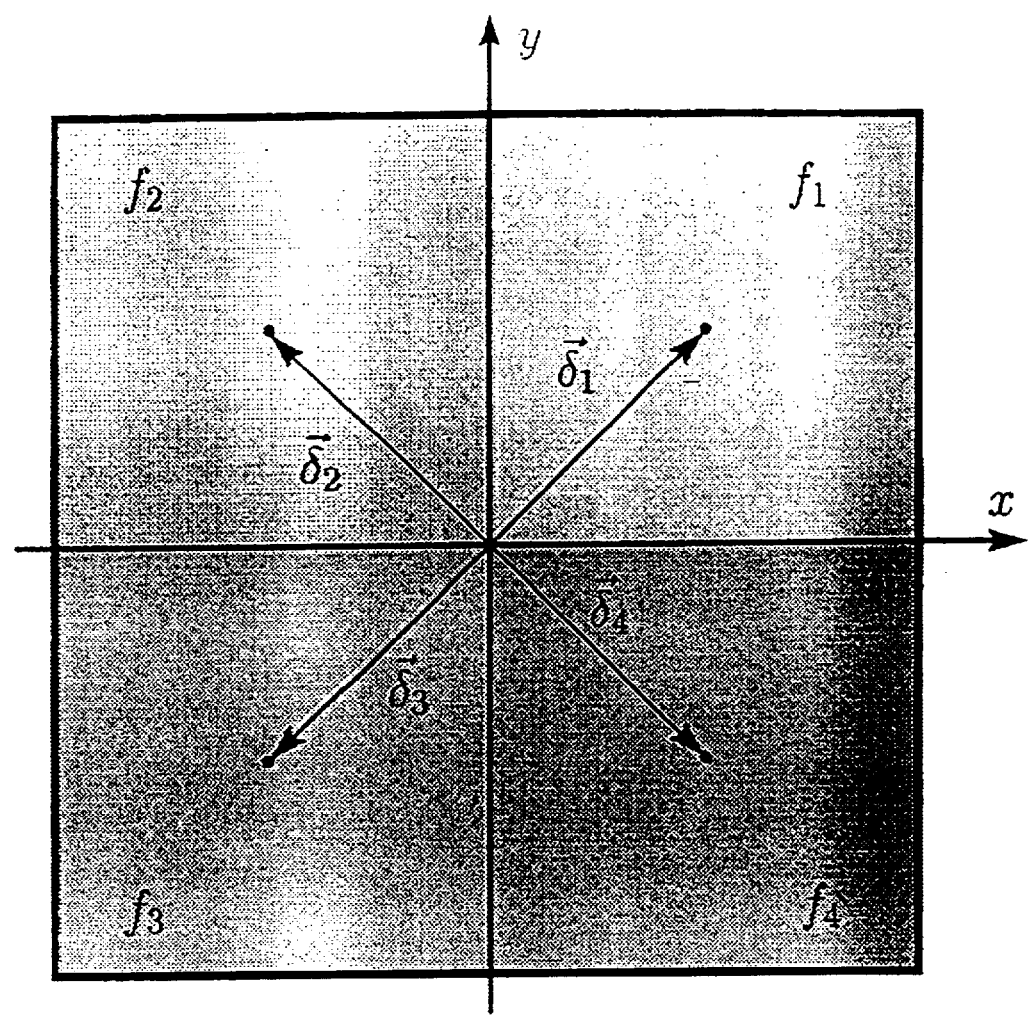
FIG. 9 is a diagram of a partition of an image into subimages.

Consider now a partition of the image f into $J=(N/M)^2$ nonoverlapping subimages, each of size M×M, $$f = \sum_{j=1}^{J} \mathcal{K}_M[\vec{\delta}_j]f, \tag{11}$$

where vectors $\vec{\delta}_j, j=1, \ldots J$ are the centers of the subimages in the global coordinate system, as shown in FIG. 9. Applying equation (10), we obtain the following exact decomposition for the backprojection, into backprojections onto the subimages.

$$f = \mathcal{B}_{N,P}[\vec{0}]g = \sum_{j=1}^{J} \mathcal{B}_{M,P}[\vec{\delta}_j]\hat{\mathcal{K}}_M[\vec{\delta}_j]g \tag{12}$$

Figure 10:
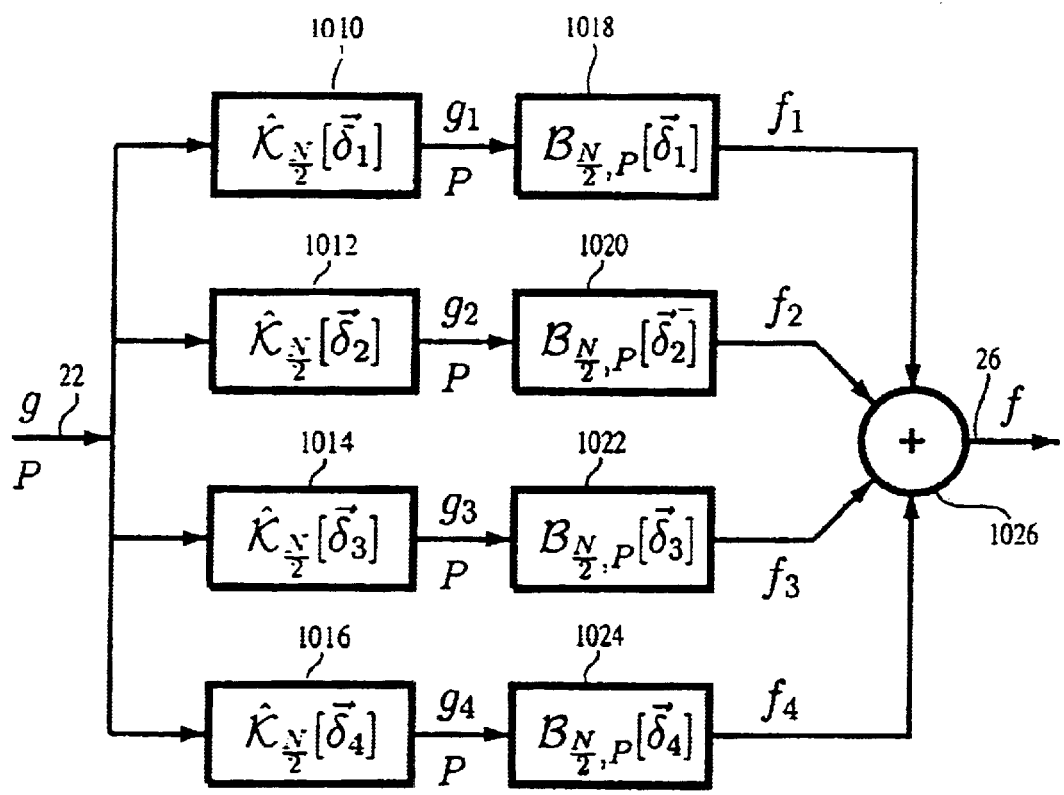
FIG. 10 is a diagram illustrating an exact decomposition of a fan-beam backprojection.

This decomposition is illustrated in FIG. 10 for N/M=2. The divergent beam sinogram₃ 22, also denoted by g in equation (12), is divided into a plurality of subsinograms corresponding to the subimages just described. The subsinograms can be any desired size, as small as one pixel or one voxel. The subsinograms, produced by truncation operators 1010, 1012, 1014 and 1016 are individually backprojected in the global coordinate system in 1018, 1020, 1022 and 1024, respectively. The backprojected sinograms produce subimages $f_1, f_2, f_3$ and $f_4$, which are aggregated at 1026 to produce the electronic image₁ 26 in FIG. 1. This process produces an exact decomposition of the fanbeam backprojection. For N/M=2, the decomposition is into four subsinograms and subimages, as illustrated in FIG. 10.

Referring again to FIG. 10, the P under the line 22 indicates the number of projections in a sinogram or subsinogram. By itself, this decomposition does not provide a speedup compared to single-step backprojection $B_{N,P}$. Indeed, while the computational cost $cM^2P$ of single subimage backprojection $B_{M,P}$ is $(N/M)^2 = J$ times smaller than for the single-step $B_{N,P}$ for the full image, the total cost for the required J such subimage backprojections remains the same (possibly with some small additional overhead for bookkeeping). The exact decomposition can still be used to provide a speedup by partitioning the backprojection between J parallel processors, or to allow the repeated use of a single processor requiring J times less memory.

The fast backprojection algorithm uses the decomposition idea with the following additional property. For fixed image resolution (bandwidth), the number of projections needed to reconstruct the image is proportional to the size of the image. That is, if P projections are needed to reconstruct an N×N image, then P'=(M/N)P projections suffice to reconstruct a M×M image to the same resolution.

The fast backprojection algorithm is therefore based on reconstruction of a subimage $f' = K_M[\vec{\delta}]f$ from a reduced number of projections. This reduction process will be performed by an operator $O[L,M,\vec{\delta}]$, which itself is composed of several operators that will now be defined.

Projection shift operators $\hat{M}_-[\vec{\delta}]$, and $\hat{M}_+[\vec{\delta}]$ that shift each projection by the amount $\pm r(\theta,\vec{\delta})$ along the t axis are defined as $$\hat{M}_-[\vec{\delta}]g(\theta,t) = g[\theta, t-\tau(\theta,\vec{\delta})]$$

$$\hat{M}_+[\vec{\delta}]g(\theta,t) = g[\theta, t+\tau(\theta,\vec{\delta})] \tag{13}$$

An L-fold angular decimation operator $D_{\downarrow L}$ reduces the number of views in a set of P projections to P/L projections, by angular filtering followed by angular subsampling. The filtering may be as simple as averaging of projections at adjacent angles, or it may also be more elaborate, and is represented by $$\tilde{g}(p,t) = h_D(p,t) * g(p,t), \tag{14}$$

where * denotes convolution and $h_D$ is the filter kernel. The filtering may occur only in p (i.e., in discrete θ) for each fixed t, or it may be combined filtering in θ and t, separable or not. The angular subsampling retains one out of every L filtered projections $\tilde{g}(p,t)$.

The operator $O[L,M,\vec{\delta}]$, a composition of the truncation, shift and angular decimation operations is then defined by $$g'(q,t) = O[L,M,\vec{\delta}]g(q,t) = \hat{M}_-[\vec{\delta}]W_2D_{\downarrow L}W_1\hat{M}_+[\vec{\delta}]\hat{K}_M[\vec{\delta}]g(q,t), \quad q=0, \ldots, P'-1, \tag{15}$$

where P'=P/L. Operator $O[L,M,\vec{\delta}]$ includes multiplicative weighting with weight functions $W_k(\theta,t), k=1,2$, before and after decimation. A possible choice might be $W_1(\theta,t)=W[\theta, \tau(\theta,\vec{\delta})]$, and $W_2(\theta,t)=1/W_1(\theta,t)$. More generally, the weighting can be chosen to optimize the accuracy of the algorithm, or omitted altogether.

Figure 11:
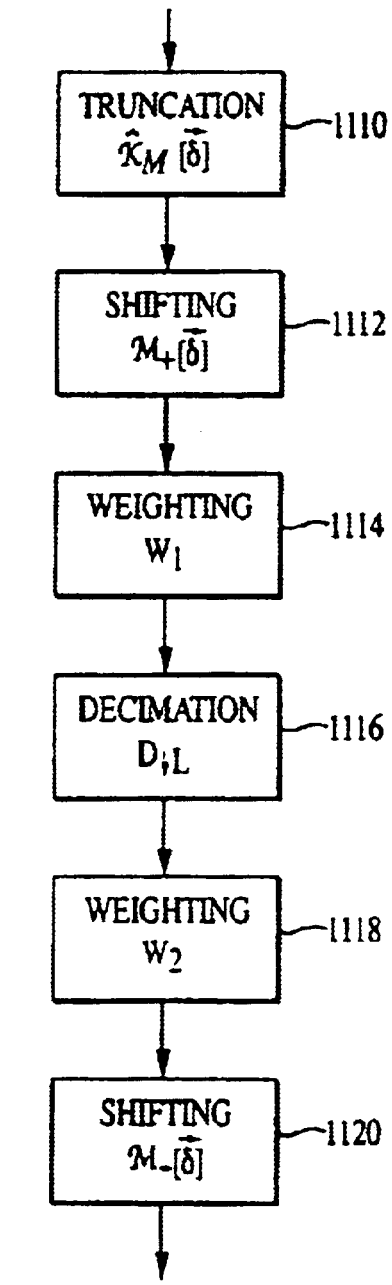
FIG. 11 is a flowchart of the process performed by the sinogram decomposition operator $O[L, M, \vec{\delta}\,]$.

FIG. 11 shows in greater detail the manner in which the subsinograms can be processed. For example, truncation $\hat{K}_M[\vec{\delta}]$ can occur first at step 1110, followed by the shifting operator $\hat{M}_+[\vec{\delta}]$ in step 1112, a weighting step 1114, followed by a decimation step 1116, another weighting step 1118, and a second shifting step 1120. This process describes the sinogram decomposition operator $O[L,M,\vec{\delta}]$.

With these definitions, the exact formula (10) for backprojection onto subimage f' is replaced by the approximation $$f' = \mathcal{K}_M[\vec{\delta}]f = \mathcal{B}_{M,P/L}[\vec{\delta}]g' \tag{16}$$

$$= \mathcal{B}_{M,P/L}[\vec{\delta}]O[L, M, \vec{\delta}]g, \tag{17}$$

where $B_{M,P/L}$ is a backprojection in the global coordinate system onto an M×M subimage using P/L projections as defined by equation (9). This leads to an approximate decomposition of the backprojection operation for a partitioned image that is analogous to equation (12), $$f = \mathcal{B}_{N,P}[\vec{0}]g = \sum_{j=1}^{J} \mathcal{B}_{M,P/L}[\vec{\delta}_j]O[L, M, \vec{\delta}_j]g. \tag{18}$$

Figure 12:
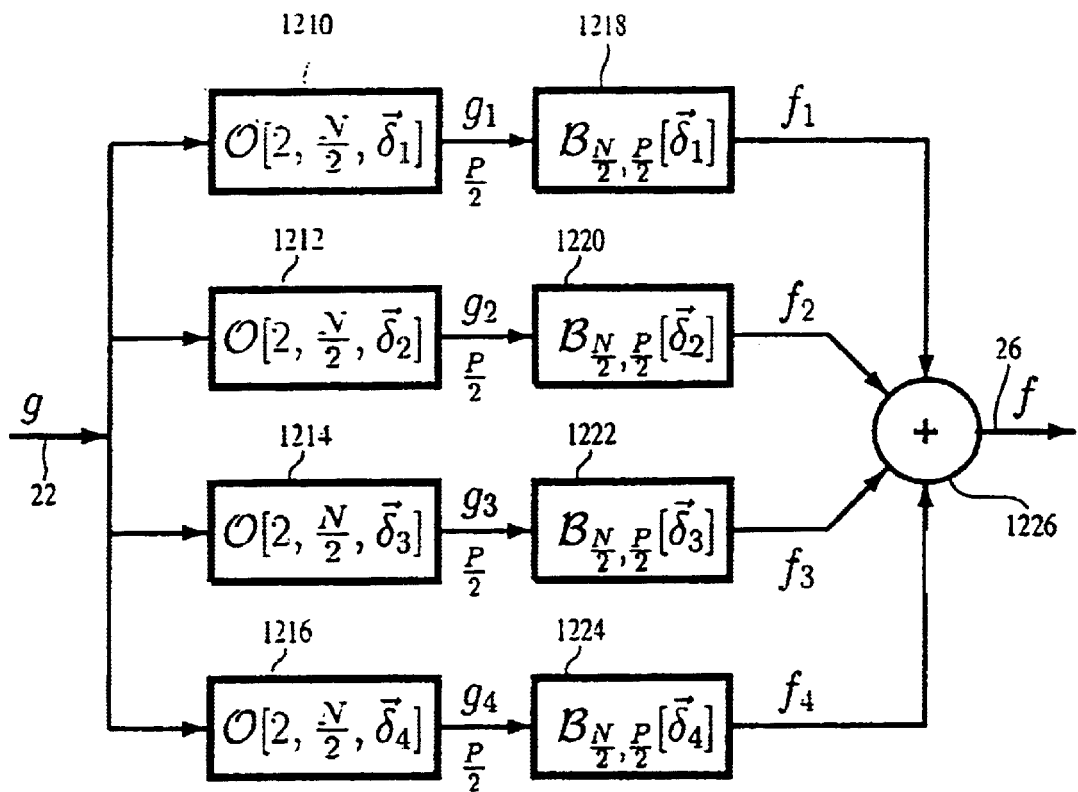
FIG. 12 is a diagram of an approximate decomposition of a fan-beam backprojection.

This decomposition is illustrated in FIG. 12, which shows an approximate decomposition for a fan-beam backprojection, with a reduction in the number of projections, for L=N/M=2. To execute the approximate decomposition, the fast backprojection processor 24 is programmed to divide the divergent beam sinogram₃, designated as g in FIG. 12 and comprising P projections four subsinograms produced by 1210, 1212, 1214 and 1216, denoted $g_1, g_2, g_3$ and $g_4$, comprising projections each. The subsinograms $g_1$, $g_2$, $g_3$ and $g_4$ are backprojected in the global coordinate system by 1218, 1220, 1222 and 1224, to produce subimages $f_1$, $f_2$, $f_3$ and $f_4$ at the correct locations in the global coordinate system. The subimages are aggregated at 1226 to produce the electronic image 26, also designated f in FIG. 12.

Referring again to FIG. 12, the number of operations for the backprojection $B_{M,P/L}$ onto each of the $J=(N/M)^2$ subimages is $cM^2$ P/L, yielding a total of $cN^2$ P/L for all backprojections. This is L times less than for single-step backprojection $B_{N,P}$. Based on the previous observation about scaling of the number of projections with image size, L can be chosen as large as L=(N/M). When the computational cost of $O[L,M,\vec{\delta}_j]$ is included, an optimum number of subimages can be determined for a single-level decomposition as shown in U.S. Pat. No. 6,263,096.

Figure 13:
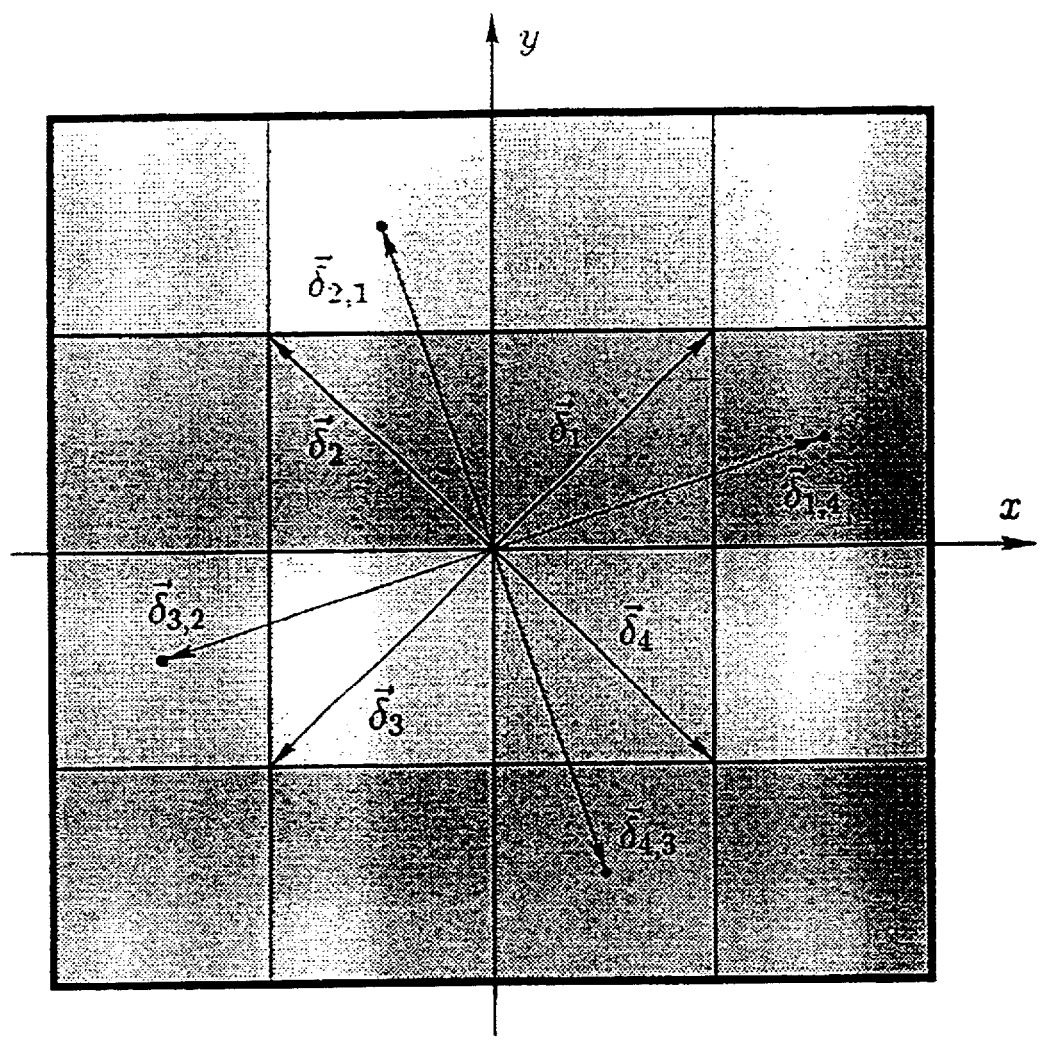
FIG. 13 is a diagram of a two-level dyadic image partition.
Figure 14:
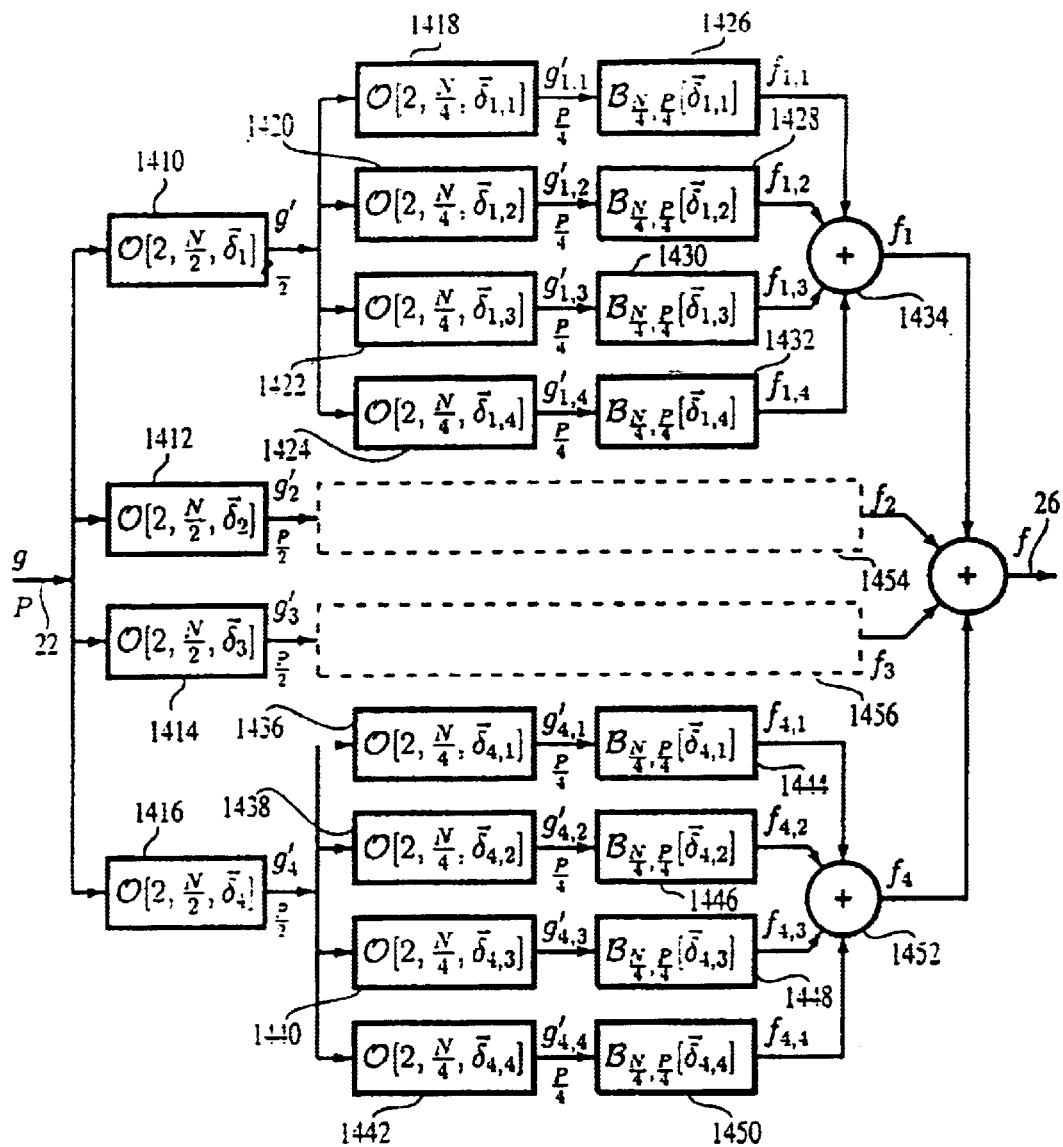
FIG. 14 is a diagram of a two-level approximate decomposition of a fan-beam backprojection.
Figure 15:
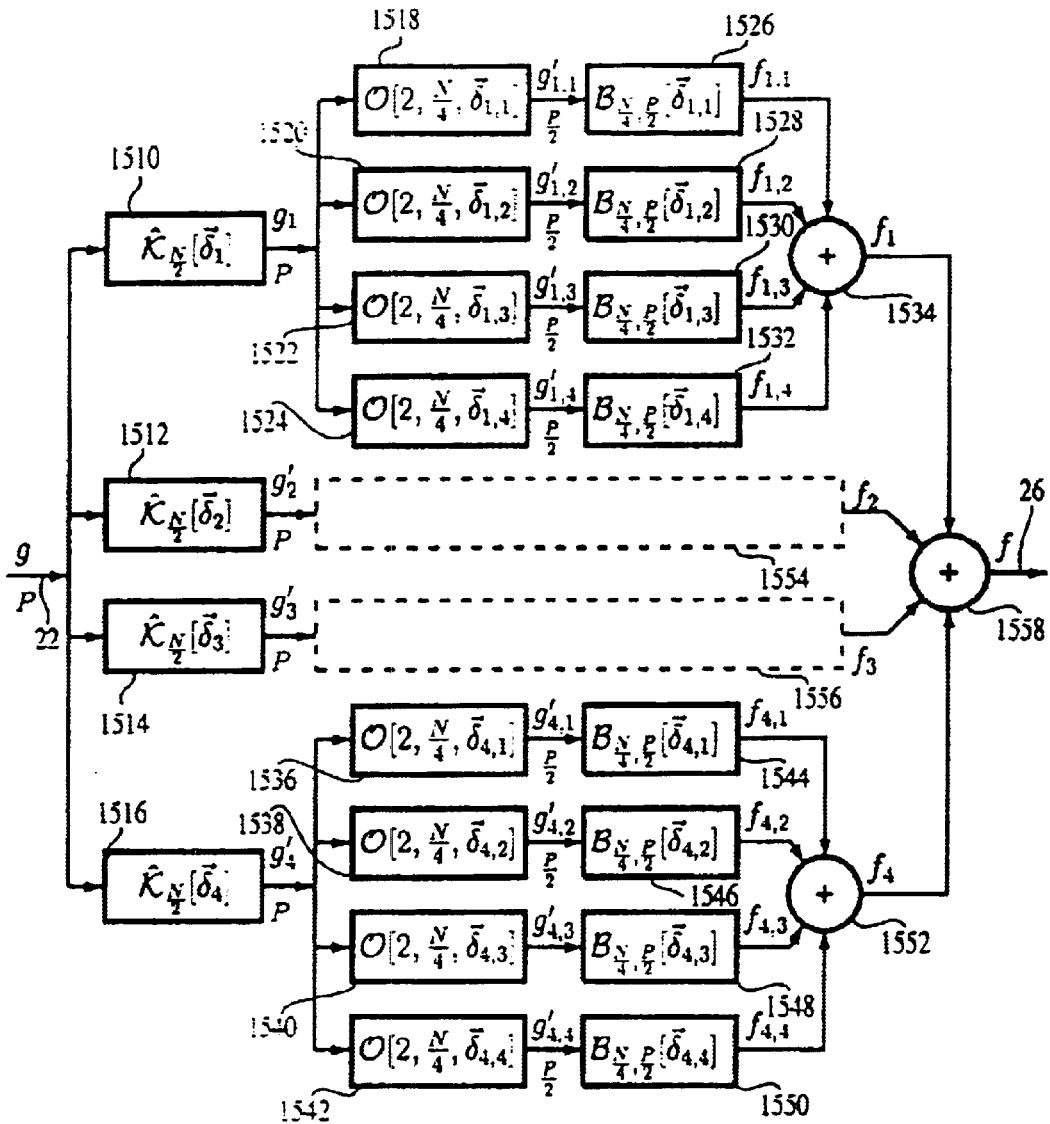
FIG. 15 is a diagram of a two-level mixed (one exact, one approximate) decomposition of a fan-beam backprojection.

In a preferred embodiment of the fast backprojection algorithm, the decompositions in equations (12) and (18) are applied recursively, at each level further partitioning the subimages into smaller subimages in accordance with equation (11). An example of a dyadic (N/M=2) two-level partitioning of the image is shown in FIG. 13. Also shown are some of the subimage center positions at the different levels. Note that they are all referenced to the zero-th level image origin O, that is, to the global coordinated system. The corresponding examples of a two-level approximate decomposition, and a two-level decomposition consisting of a cascade of one exact decomposition and one approximate decomposition are shown in FIGS. 14 and 15, respectively. In FIG. 14, the divergent-beam sub-sinogram$_3$ 22 comprising P projections, is processed in the fast backprojection processor 24 by dividing the sinogram into subsinograms 1410, 1412, 1414 and 1416, each comprising P/2 projections. This approximate subdivision is performed by the approximate decomposition operator described by the flowchart of FIG. 11. Further approximate decompositions of the subsinogram 1410 are generated at 1418, 1420, 1422 and 1424, again using the operator described by the flowchart of FIG. 11, but this time with different parameters, corresponding to the smaller subimages in FIG. 13. Each of those subsinograms, comprising P/4 projections, is backprojected in the global coordinate system at 1426, 1428, 1430 and 1432 to produce a plurality of subimages $f_{1,1}$, $f_{1,2}$, $f_{1,3}$, $f_{1,4}$ at the correct locations in the global coordinate system shown in FIG. 13. The subimages are aggregated at 1434 to produce a subimage $f_1$—also at the correct location in the global coordinate system.

The subsinogram represented by 1416 is similarly subdivided at 1436, 1438, 1440 and 1442. Those subsinograms are backprojected at 1444, 1446, 1448 and 1450, respectively, and are aggregated at 1452 to produce subimage $f_4$. The dotted boxes 1454 and 1456 represent the corresponding level-2 decompositions for $f_2$ and $f_3$, respectively. In FIG. 14 all of the decompositions are approximate decompositions of a fan-beam projection for L=N/M=2.

FIG. 15 illustrates a two-level mixed (one exact, one approximate) decomposition of a fan-beam projection for L=N/M=2. In FIG. 15, the sinogram 22, comprising P projections, is decomposed into exact subsinograms 1510, 1512, 1514 and 1516, also comprising P projections each. The exact subsinograms, designated $g_1$, $g_2$, $g_3$ and $g_4$ respectively, are decomposed, using the approximate decomposition operator illustrated in FIG. 11 (with appropriate parameters), into approximate subsinograms, each comprising P/2 projections. For example, $g_1$ is decomposed at 1518, 1520, 1522 and 1524 to produce approximate subsinograms $g_{1,1}$, $g_{1,2}$, $g_{1,3}$ and $g_{1,4}$. Those subsinograms are backprojected in the global coordinate system at 1526, 1528, 1530 and 1532 to produce subimages $f_{1,1}$, $f_{1,2}$, $f_{1,3}$ and $f_{1,4}$, at the correct locations in the global coordinate system. Those subimages are aggregated at 1534 to produce a subimage $f_1$.

The subsinogram produced at 1516, designated $g_4$ in FIG. 15, is also further decomposed into four subsinograms at 1536, 1538, 1540 and 1542 to produce subsinograms $g_{4,1}$, $g_{4,2}$, $g_{4,3}$ and $g_{4,4}$. Backprojections at 1544, 1546, 1548 and 1550 produce subimages $f_{4,1}$, $f_{4,2}$, $f_{4,3}$ and $f_{4,4}$, which are aggregated at 1552 to produce a subimage $f_4$. The dotted boxes 1554 and 1556 represent the corresponding two-level mixed decomposition for $g_2$ and $g_3$, respectively. Those processes produce subimages $f_2$ and $f_3$, and the subimages $f_1$, $f_2$, $f_3$ and $f_4$ are aggregated at 1558 to produce the image 26, designated f in FIG. 15.

The recursion can be continued until the subimages are of some desired minimum size $M_{min}$, and then the backprojections $B_{P_{min},M_{min}}$ performed in the global coordinate system using equation (5). The optimum $M_{min}$ is usually implementation-dependent. It can be chosen as small as $M_{min}=1$, so that the smallest subimages are 1 pixel or voxel in size. Assuming N is a power of two and N/M=2 at all levels of the decomposition, there will be $\log_2 N$ such levels. Assuming further L=(N/M)=2 and P=kN, with k a small integer, the last level will involve $N^2$ single pixel backprojections $B_{P/N,1}$, with a total cost of cPN. Assuming fixed length interpolators are used for the decimation and shift operations in the implementation of $O[L,M,\vec{\delta}_j]$, it can be shown that the computation cost of each level will be $c_1 NP$, where $c_1$ is a constant. The total cost of the $\log_2 N$ levels is therefore $O(PN \log N)$, and because P=O(N), the total cost of the recursive decomposition algorithm becomes $O(N^2 \log N)$.

In practice, projection data are sampled in t with interval $\Delta t$, because of the use of discrete detectors. Thus, the projection shift operators $\hat{M}_-[\vec{\delta}]$, and $\hat{M}_+[\vec{\delta}]$ will be implemented in discrete form, but will require shifts by noninteger multiples of $\Delta t$. Because the projections have been filtered before backprojection, they are bandlimited, and can be shifted using a combination of interpolation and resampling, e.g., as described in U.S. Pat. No. 6,287,257. In particular, shifting by noninteger multiples of $\Delta t$ can be separated into shifting by integer multiples of $\Delta t$, cascaded with shifting by a fraction of $\Delta t$. The integer shifts correspond to simple re-indexing, whereas the fractional shifts can be performed by interpolation in the t variable. Furthermore, this interpolation can be executed by the radial filtering corresponding to the convolution in the radial dimension with the filter $h_D(p,t)$ in the generalized decimation filtering step in equation (14).

Importantly, with the specific projection-shifting scheme proposed here, the sampling interval of the projections remains uniform and constant, so that the interpolation and resampling can be performed as a discrete-to-discrete mapping and efficiently implemented as a simple digital filter. The error involved in such fractional t-shifting can be made to decay exponentially with the length of the interpolator, so that short interpolators—even simple linear interpolation—usually suffice. The t-interpolation accuracy also increases by oversampling the projections in t, which, if desired, can be performed efficiently by digital interpolation (upsampling followed by filtering) of the projections.

The accuracy of the backprojection obtained using the approximate decomposition depends on the various parameters in the process, including P,N,M,L, the resolution in the image and bandwidth of the projections, maximum fan angle of source rays intersecting the object, detector response, and the interpolators used in the algorithm. These parameters can be appropriately optimized in the divergent beam algorithms. An important parameter affecting accuracy is the ratio (P/L)/M between the number of projections used in the backprojections, and the size of the subimages. By increasing this ratio, also called angular oversampling, the accuracy of the approximate decomposition is increased.

There are several ways to increase the angular oversampling, including the following: (i) digital angular interpolation of the projections g to increase P before the start of the decomposition; (ii) choosing L<(N/M) at various stages of the approximate decomposition; and (iii) using exact decomposition steps, e.g., as shown in the example in FIG. 15. To understand Method (iii), recall that the exact decomposition in equation (12) reduces the size of the subimages, but not the number of projections in a subsinogram. Thus, it leads to an increase in angular oversampling by the factor (N/M), and improved accuracy.

In fact, apart from implementation details, which may give one of the methods, (ii), or (iii), a small computational advantage over the other, method (iii) for angular oversampling is equivalent to method (ii) because of the identity $\hat{K}_{M/2}[\vec{\delta}_{ij}]\hat{K}_M[\vec{\delta}_i]=\hat{K}_{M/2}[\vec{\delta}_{ij}]$ which holds whenever $\vec{\delta}_{ij}$ is the center of a subimage of the subimage centered at $\vec{\delta}_i$. It follows, therefore, that the two-stage decomposition with dyadic partitioning, one exact and one approximate, is equivalent to a single approximate decomposition into 16 subimages of size N/4 each, with decimation L=2, instead of the maximum possible of L=4. Thus, both methods provide the same factor of 2 angular oversampling. On the other hand, by choosing L=3, the single-level approximate decomposition into 16 subimages can provide a factor of 4/3 angular oversampling, thus providing additional flexibility in choice of operating point. In general, methods to increase angular oversampling lead to an increase in the computational cost of the algorithm by a constant factor. Thus, they provide ways to control the tradeoff between computation and accuracy.

A preferred embodiment of the algorithm includes a number of exact subdivisions, and a number of approximate subdivisions, or approximate subdivision with decimation factors smaller than their subdivision factors. The number of exact subdivisions and/or the decimation factors control the oversampling factor, and are chosen to obtain the desired tradeoff between computation and accuracy.

The simplest embodiment would use a subdivision by a constant factor of N/M=2 at each level, with L=2 in the approximate subdivision levels, but other choices are possible of course.

As presented, the algorithm requires P divisibility by the product of decimation factors L in all levels. When this can not be conveniently or effectively achieved by choice of the decimation factors, P can be modified by angular interpolation and resampling of the projections.

To further illustrate the recursive structure of the preferred embodiment of the algorithm, an example of the pseudo-code for the algorithm written as a recursive function, for M/N=L=2, is shown in FIG. 16. While the pseudo-code is self-explanatory, it will described briefly.

The function FAN_FHBP is a recursive function operating, in the first top-level invocation call on the full sinogram G. In subsequent calls to itself, this function decomposes the image into subimages and performs sinogram decompositions until a minimum image size $N_{min}$ is reached. Q of these decompositions are exact, the rest approximate. When the image size $N_{min}$ is reached, an exact backprojection in the global coordinate system is performed on the sub-sinogram corresponding to the subimage. For subimages bigger than $N_{min}$, the projections are truncated to correspond to the subimage. This constitutes the exact singram subdivision. When the exact decompositions are completed (when Q<1), the additional steps for approximate decompositions are performed. In FIG. 16, the projections are shifted, weight-decimated and shifted again. The subimages are aggregated at $$\text{FAN\_FHBP} = f = \sum_{i=1}^{4} f_i.$$

Subimage centers are also computed recursively, with the center $\vec{\delta}_i$ of subimage i of a bigger subimage centered at $\vec{\delta}$, expressed as $\vec{\delta}_i = \vec{\delta} + \vec{\xi}_i$, where $\vec{\xi}_i$ is the appropriate position vector of subimage $f_i$ relative to $\vec{\delta}$. The center of the full-size image is, by definition, at the origin of the global coordinate system. Thus all subsequent subimage centers are expressed in the global coordinate system.

In a preferred embodiment of the fast backprojection algorithm, the recursive decompositions are simplified by the following observation. The operations of projection shift in t, projection truncation, and projection weighting commute (with appropriate coordinate transformations). Therefore, the operations $\hat{M}_-[\vec{\delta}_i]W_{2,i}$ of one stage, can be combined with $W_{1,ij}\hat{M}_+[\vec{\delta}_{ij}]$ of the following stage into one shift and one weighting operation. Likewise, the shifting and weighting operations $\hat{M}_-[\vec{\delta}_i]W_{2,i}$ occurring just before the final subimage backprojection $B_{M_{min},P_{min}}$ can be combined with the weighting and interpolation operations in the backprojection itself. Thus, in a recursive implementation, O[L, M, $\vec{\delta}_j$] requires only one projection shift step, and (at most) one weighting per stage.

As would be apparent to a person skilled in signal processing algorithm design and implementation, the various operations defining the processes of this invention can be rearranged in various orders different from those described by the figures presented herein, or executed in parallel, without changing the function or the principles of the process. Some such rearrangements may be advantageous from an implementation, operation, or cost viewpoint. For example, the operation of decimating the number of projections for a subimage can begin as soon as two or more projections have been truncated and shifted for this subimage, without waiting for all P projections to be truncated and shifted. Such rearrangements can be used to pipeline the reconstruction algorithm, and overlap it with data acquisition.

Furthermore, the methods of this invention can be applied to continuously update tomographic imagery as projections are acquired sequentially in time. This can be accomplished by using the proposed method to backproject a sinogram consisting of the difference between the most recently acquired projections and an older set of projections. The backprojection result is then added to the current image to produce the updated image. Such updates can continue in a sequential manner.

Fast Reprojection

Backprojection and reprojection are dual operations, or the adjoint of one another. The fast native fan-beam algorithms for their implementation are therefore closely related. Therefore, the fast native fan-beam reprojection algorithm will be described in somewhat less detail, with the understanding that all discussion of the fast backprojection algorithm has an analog in the reprojection algorithm.

Consider the M×M subimage $f'=K_M[\vec{\delta}]f$ of f, shown in FIG. 8. Its fan-beam projections at source angles $\theta_q = q\Delta\theta$, $q=0 \ldots Q-1$ are $$g(q,t) = P_{M,Q}[\vec{\delta}]f'(q,t) = (PK_M[\vec{\delta}]f)(q,t). \tag{19}$$

We denote by $P_{M,Q}[\vec{\delta}]$ the associated reprojection operator in the global coordinate system for the M×M subimage with center at location $\vec{\delta}$. In particular, $(Pf) = P_{N,P}[\vec{0}]f$ are the fan-beam projections of the entire image. The computational cost of $P_{M,Q}$ is $cM^2Q$ for some constant c.

Consider next the image partition of equation (11) illustrated in FIG. 9. Because of the linearity of the projection operator, the following exact decomposition of reprojection into the sum of J reprojections of smaller M×M images for the same number P of source angles can be obtained as follows:

$$(Pf) = \sum_{j=1}^{J} \mathcal{P}_{M,P}[\vec{\delta}_j] \mathcal{K}_M[\vec{\delta}_j]f. \tag{20}$$

Figure 17:
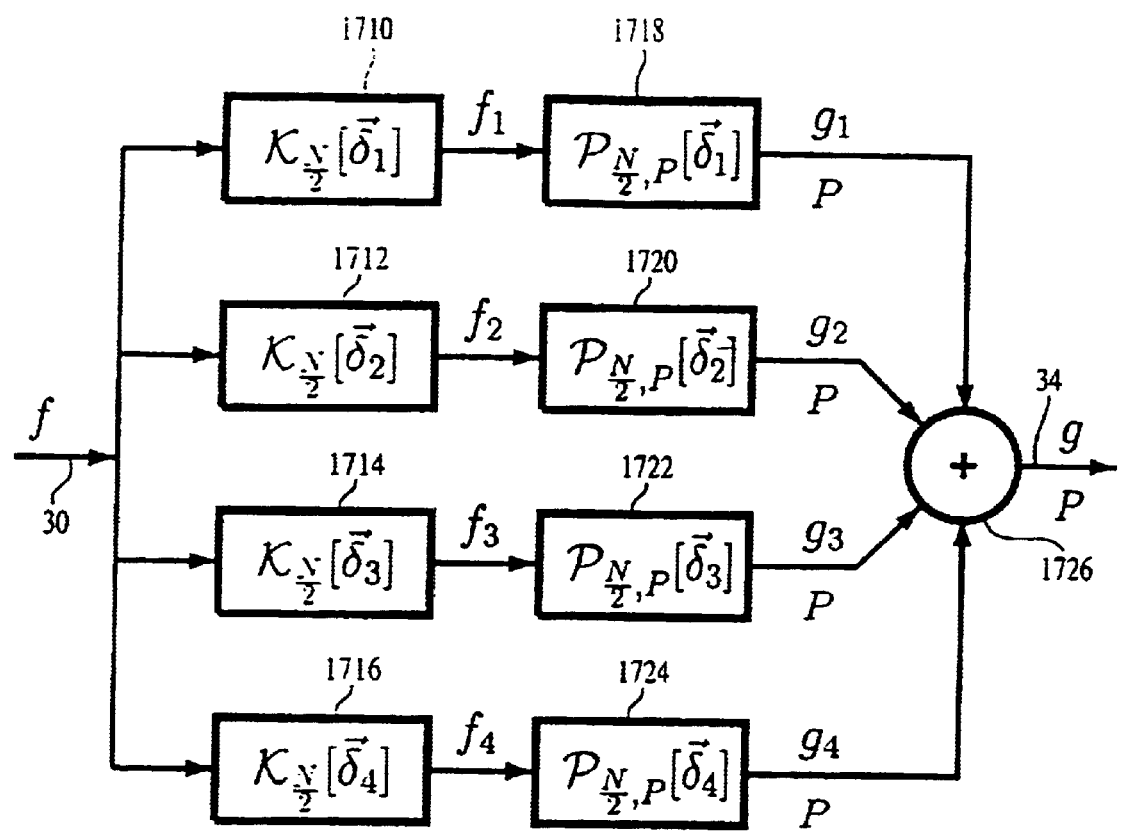
FIG. 17 is a diagram illustrating an exact decomposition of a fan-beam reprojection.

This exact decomposition for reprojection is illustrated in FIG. 17 for N/M=2. In FIG. 17, the electronic image₂ 30, also designated f in FIG. 17, is subdivided by truncation operators 1710, 1712, 1714 and 1716, into subimages $f_1, f_2, f_3$ and $f_4$, respectively. The subimages are reprojected in the global coordinate system by 1718, 1720, 1722 and 1724 to produce subsinograms $g_1, g_2, g_3$ and $g_4$. The subsinograms are aggregated at 1726 to produce the sinogram 34, also designated g in FIG. 17.

For the same reasons as in the case of the exact decomposition of equation (12) of backprojection, this decomposition of the reprojection does not provide a speedup compared to the single-step backprojection $(Pf)=P_{N,P}[\vec{0}]f$, but it has other possible applications, in particular in combination with the approximate decomposition.

The fast reprojection algorithm uses the decomposition idea with the following additional property mentioned earlier: for fixed image resolution (bandwidth), the number of fan-beam projections characterizing the image, or, equivalently, the bandwidth of the projections in the θ variable, is proportional to the size of the image. Thus, if P projections characterize an N×N image f, then P'=P/(N/M) projections characterize a subimage f', and the rest of the projections can be obtained from this smaller set.

Figure 18:
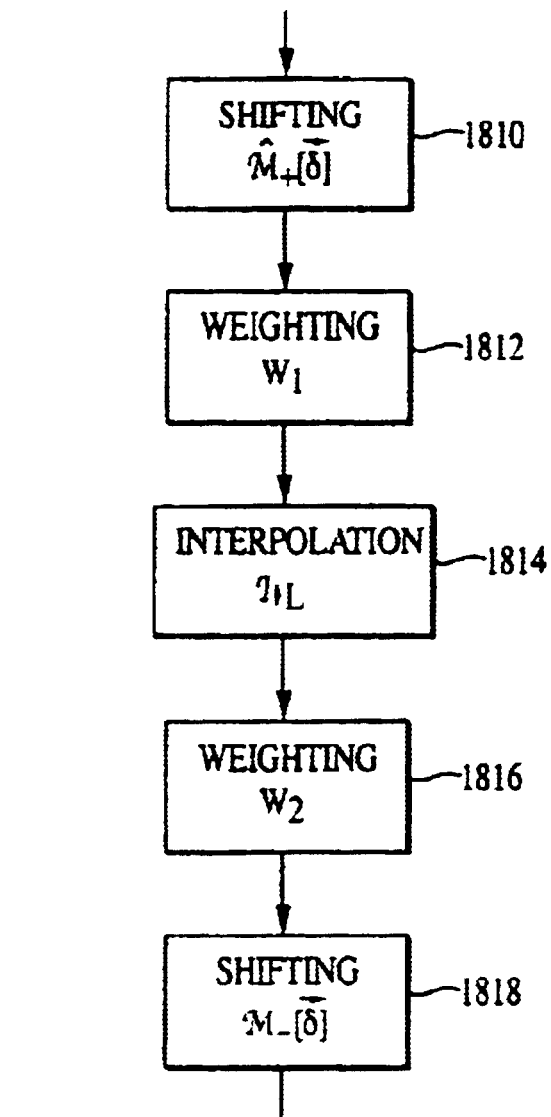
FIG. 18 is a flowchart of the process performed by the projection augmentation operator $\upsilon[L, M, \vec{\delta}\,]$.

The fast reprojection algorithm is therefore based on calculating a set of P' projections of a M×M subimage f', and using a "projection augmentation process" to obtain the larger set of P projections. This augmentation process will be performed by an operator $v[L,M,\vec{\delta}]$, which itself is composed of several operators. The projection shift operators $\hat{M}_-[\vec{\delta}]$ and $\hat{M}_+[\vec{\delta}]$ are as defined earlier in equation (13). The L-fold angular interpolation operator $I_{\uparrow L}$ increases the number of views in a set of Q projections to QL projections, by L-fold angular upsampling followed by angular filtering. The angular upsampling introduces L-1 zero-valued projections between every two projections. Denoting by g(p,t) the upsampled projections, the filtering is as described by equation (14) and the associated discussion. The resulting angular interpolation operator $I_{\uparrow L}$ is the adjoint of the angular decimation operator $D_{\downarrow L}$ arising in the fast backprojection algorithm. The projection augmentation operator $v[L,M,\vec{\delta}]$, a composition of the shift and angular interpolation operations, is then defined by $$g'(p,t) = v[L,M,\vec{\delta}]g(q,t) = \hat{M}_-[\vec{\delta}]W_2 I_{\uparrow L} W_1 \hat{M}_+[\vec{\delta}]g(q,t), \; p=0, \ldots P'-1, \tag{21}$$

where P'=QL. Operator $v[L,M,\vec{\delta}]$ includes multiplicative weighting with weight functions $W_k(\theta,t), k=1,2$ before and after interpolation, with similar function and selection criteria as for $O[L,M,\vec{\delta}]$. For example, as seen in FIG. 18, a first shifting function 1810 can be followed by a first weighting function 1812, and interpolation function 1814, a second weighting function 1816 and a second shifting function 1818. Other combinations of projection augmentation operators can be used, if preferred.

With these definitions, the approximate reprojection of subimage f' is $$g' = P_{M,P}[\vec{\delta}]f' = v[L,M,\vec{\delta}]P_{M,P/L}[\vec{\delta}]f' \tag{22}$$

where $P_{M,P/L}$ is a reprojection in the global coordinate system computing only P/L projections. This leads to an approximate decomposition of the reprojection operation for a partitioned image that is analogous to equation (20), $$g = \mathcal{P}_{N,P}[\vec{0}]f = \sum_{j=1}^{J} \mathcal{V}[L,M,\vec{\delta}_j] \mathcal{P}_{M,P/L}[\vec{\delta}_j] \mathcal{K}_M[\vec{\delta}_j]f. \tag{23}$$

Figure 19:
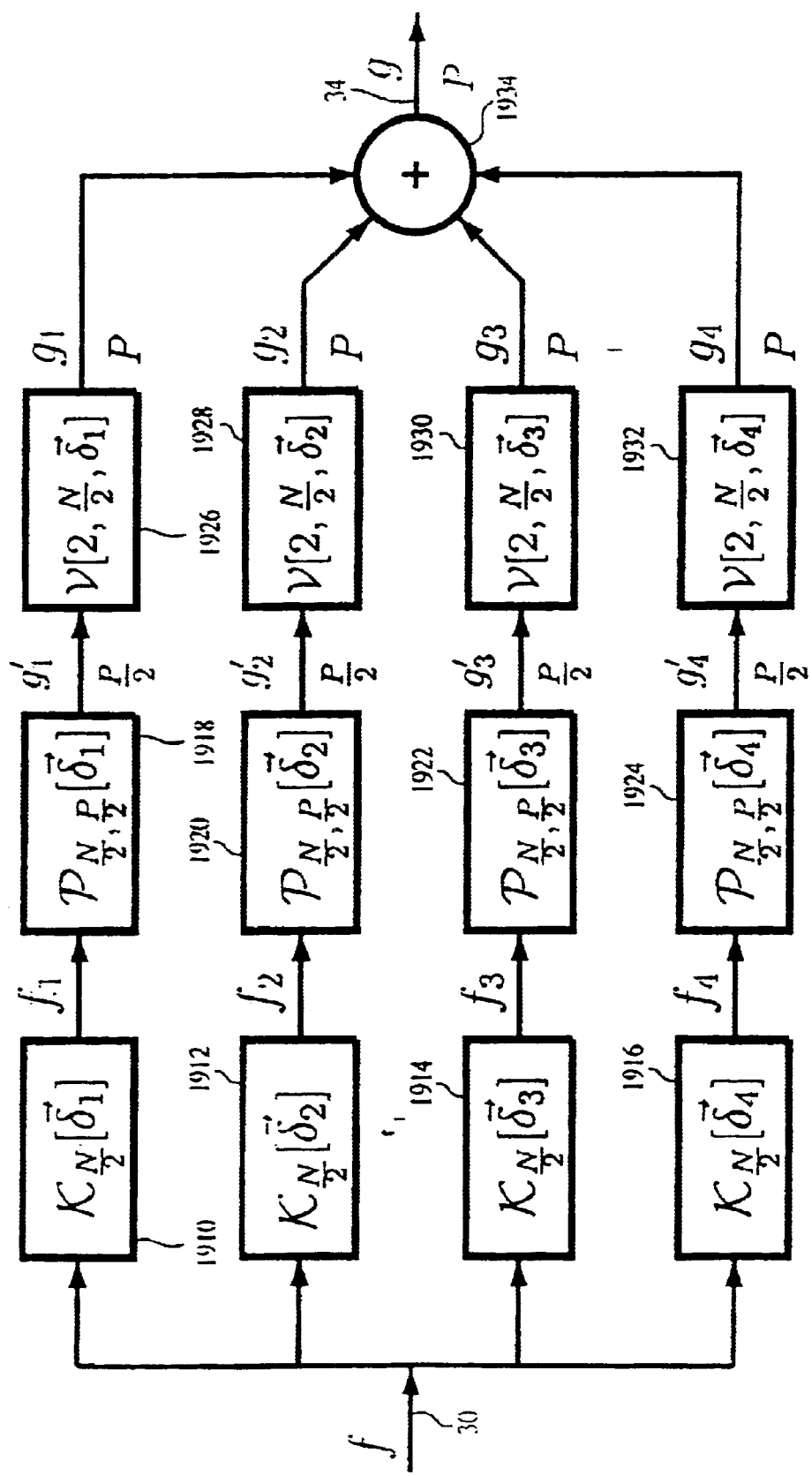
FIG. 19 is a diagram of an approximate decomposition of a fan-beam reprojection.

This approximate decomposition is illustrated in FIG. 19 for L=N/M=2. In FIG. 19, the fast reprojection processor 32 from FIG. 1 is programmed to accept the electronic image₂ 30, also designated f in FIG. 19, and divide in 1910, 1912, 1914 and 1916 to into subimages $f_1, f_2, f_3$ and $f_4$, respectively. Reprojections in the global coordinate system are performed at 1918, 1920, 1922 and 1924 to produce subsinograms $g_1, g_2, g_3,$ and $g_4$, respectively, with P/2 projections each. The subsinograms are augmented at 1926, 1928, 1930 and 1932, as previously described, and the resulting subsinograms $g_1, g_2, g_3,$ and $g_4$ with P projections each are aggregated at 1934 to produce the sinogram 34, also designated g in FIG. 19.

As in the case of the approximate decomposition of the backprojection, the computational cost is L-fold smaller than the single step reprojection $P_{N,P}$, and the same discussion applies.

Figure 20:
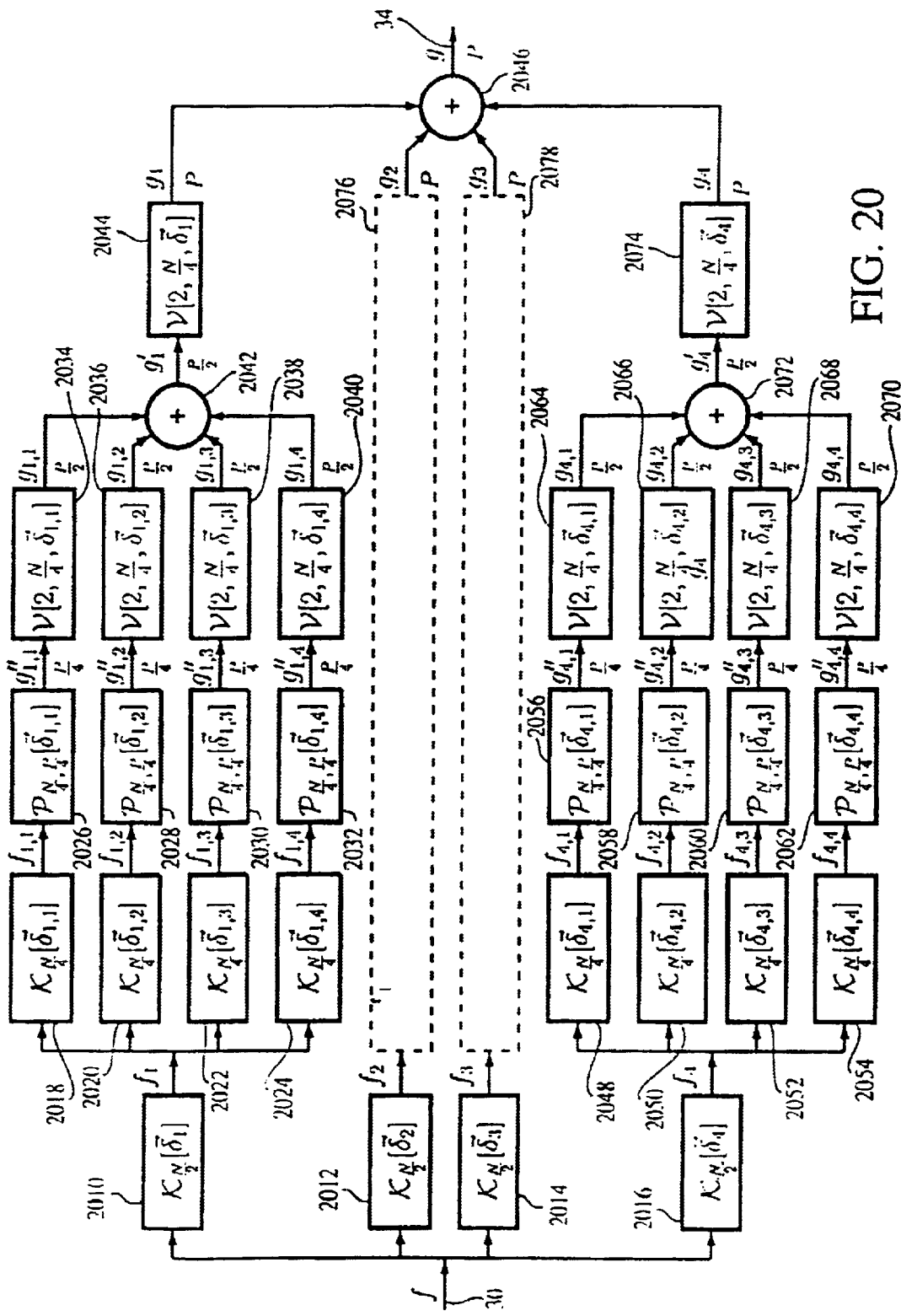
FIG. 20 is a diagram of a two-level approximate decomposition of a fan-beam reprojection.
Figure 21:
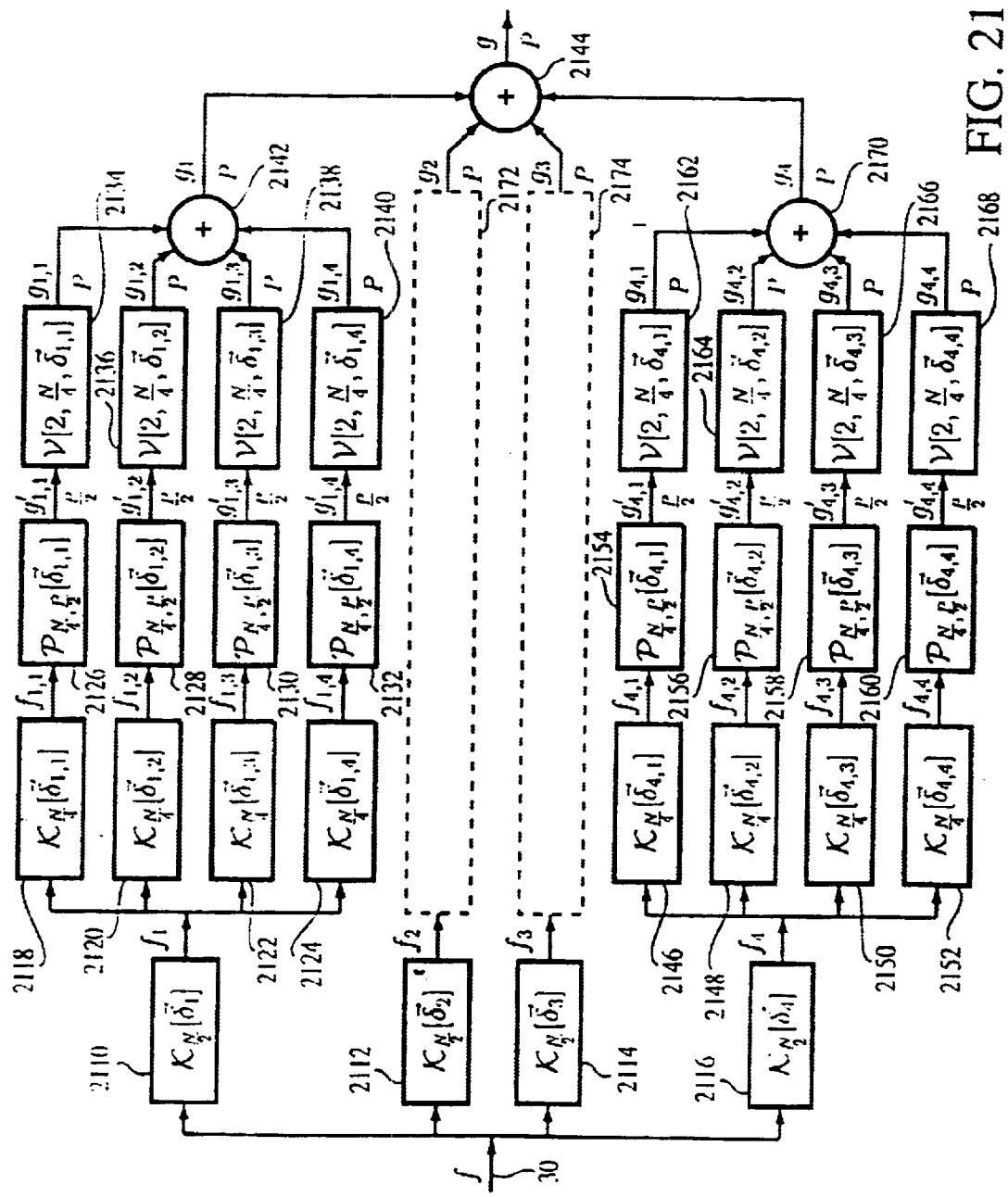
FIG. 21 is a diagram of a two-level mixed (one exact, one approximate) decomposition of a fan-bream reprojection.

In a preferred embodiment of the fast reprojection algorithm the decompositions in equations (20) and (23) are applied recursively, at each level further partitioning the subimages into smaller subimages in accordance with equation (11), and illustrated in FIG. 13. The corresponding examples of a two-level approximate decomposition, and a two-level decomposition consisting of a cascade of one exact decomposition and one approximate decomposition are shown in FIGS. 20 and 21, respectively. In FIG. 20, a two-level approximate decomposition of a fan-beam reprojection for L=N/M=2 begins with the electronic image₂ 30, also designated f in FIG. 20. The image f is divided into subimages $f_1, f_2, f_3$ and $f_4$ at 2010, 2012, 2014 and 2016, respectively, and the subimage $f_1$ is further subdivided into subimages $f_{1,1}, f_{1,2}, f_{1,3}$ and $f_{1,4}$ at 2018, 2020, 2022 and 2024. Those subimages are reprojected in the global coordinate system by 2026, 2028, 2030 and 2032, respectively, to produce subsinograms $g_{1,1}$, $g_{1,2}$, $g_{1,3}$ and $g_{1,4}$, comprising P/4 projections each. The subsinograms are augmented by 2034, 2036, 2038 and 2040, to produce subsinograms $g_{1,1}$, $g_{1,2}$, $g_{1,3}$ and $g_{1,4}$, comprising P/2 projections each, which are aggregated at 2042 to produce a subsinogram $g_1$ comprising P/2 projections. After additional augmentation at 2044, the subsinogram $g_1$, comprising P projections, is aggregated with subsinograms $g_2$, $g_3$ and $g_4$ at 2046.

The subimage $f_4$ is further decomposed at 2048, 2050, 2052 and 2054 and the subimages are similarly reprojected at 2056, 2058, 2060 and 2062 to produce subsinograms $g_{4,1}$, $g_{4,2}$ and $g_{4,3}$ and $g_{4,4}$, respectively. After augmentation at 2064, 2066, 2068 and 2070, the resulting subsinograms $g_{4,1}$, $g_{4,2}$ and $g_{4,3}$ and $g_{4,4}$ are aggregated at 2072 and the resulting subsinogram is further augmented at 2074. The resulting subsinogram $g_4$ is aggregated with the other subsinograms at 2046 to produce the subsinogram 34 in FIG. 1, also designated g in FIG. 20. The dotted boxes 2076 and 2078 represent the corresponding level-2 decompositions for $f_2$ and $f_3$, respectively.

FIG. 21 illustrates a two-level mixed (one exact, one approximate) decomposition of a fan-beam reprojection for L=N/M=2. In FIG. 21, the electronic image₂ 30 from FIG. 1, also designated f in FIG. 21, is decomposed into subimages $f_1$, $f_2$, $f_3$ and $f_4$, by 2110, 2112, 2114 and 2116, respectively. The subimage $f_1$ is subdivided into subimages $f_{1,1}$, $f_{1,2}$, $f_{1,3}$ and $f_{1,4}$, by 2118, 2120, 2122 and 2124. The subimages are reprojected in the global coordinate system by 2126, 2128, 2130 and 2132 to produce subsinograms $g_{1,1}$, $g_{1,2}$ and $g_{1,3}$ and $g_{1,4}$ comprising P/2 projections each. Subsinograms $g_{1,1}$, $g_{1,2}$, $g_{1,3}$ and $g_{1,4}$, comprising P projections each are produced after augmentation by 2134, 2136, 2138 and 2140. Aggregation at 2142 produces a subsinogram $g_1$, comprising P projections, which is aggregated with subsinograms $g_2$, $g_3$ and $g_4$ at 2144 producing sinogram g comprising P projections. Similarly, the subimage $f_4$ is further subdivided at 2146, 2148, 2150 and 2152 to produce subimages $f_{4,1}$, $f_{4,2}$, $f_{4,3}$ and $f_{4,4}$. Reprojection by 2154, 2156, 2158 and 2160 produces subsinograms $g_{4,1}$, $g_{4,2}$ and $g_{4,3}$ and $g_{4,4}$, which are augmented by 2162, 2164, 2166 and 2168 to produce subsinograms $g_{4,1}$, $g_{4,2}$ and $g_{4,3}$ and $g_{4,4}$. Those subsinograms are aggregated at 2170 to produce the subsinogram $g_4$. The dotted boxes 2172 and 2174 represent the corresponding level-2 decompositions for $g_2$ and $g_3$, respectively.

The recursion can be continued until the subimages are of some desired minimum size $M_{min}$, and then the reprojections $P_{P_{min},M_{min}}$ computed using equation (7).

The following considerations for the fast reprojection algorithm are analogous to those discussed for the case of backprojection:

1. Choice of various parameters in the fast reprojection algorithm, including P,N,M,L and $M_{min}$.
2. Handling the discreteness in t.
3. Use of angular oversampling and the combination of exact and approximate decomposition steps to control the tradeoff between accuracy and speed.
4. Simplification of the sequences of operators $\hat{M}_{-}[\vec{\delta}_i]W_{2,i}$ and $W_{1,ij}\hat{M}_{+}[\vec{\delta}_{ij}]$ by combining shifting and weighting operations between successive stages, resulting in a single shifting and (at most) a single weighting operation per stage.
5. Possible rearrangements of the order of operations.
6. The $O(N^2 \log N)$ computational complexity of the resulting hierarchical reprojection algorithm.

Fast Native Algorithms for Equiangular Fanbeam Geometry

Figure 22:
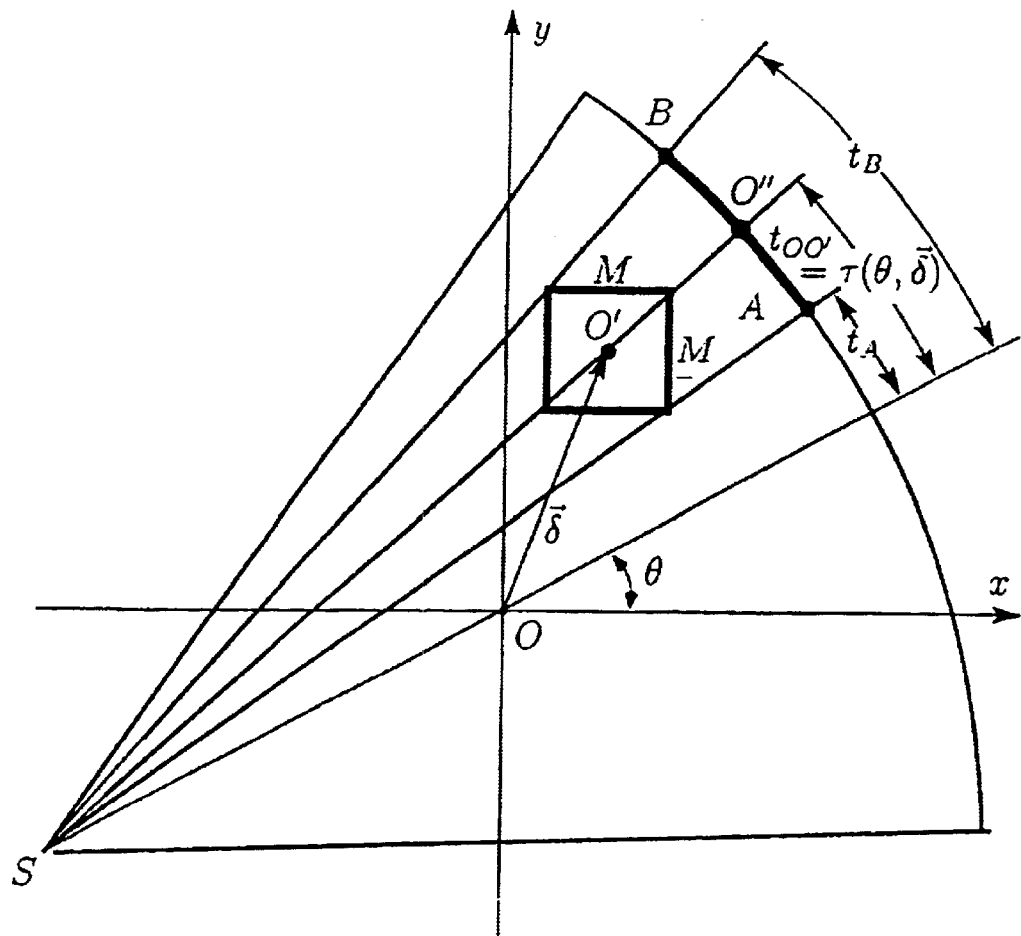
FIG. 22 is a diagram of an equiangular fan-beam projection geometry for a subimage.

For the equiangular detector case, a similar scheme can be applied to hierarchically decompose the image to smaller subimages. FIG. 22 illustrates the projection geometry for subimage f' in this case.

Figure 6:
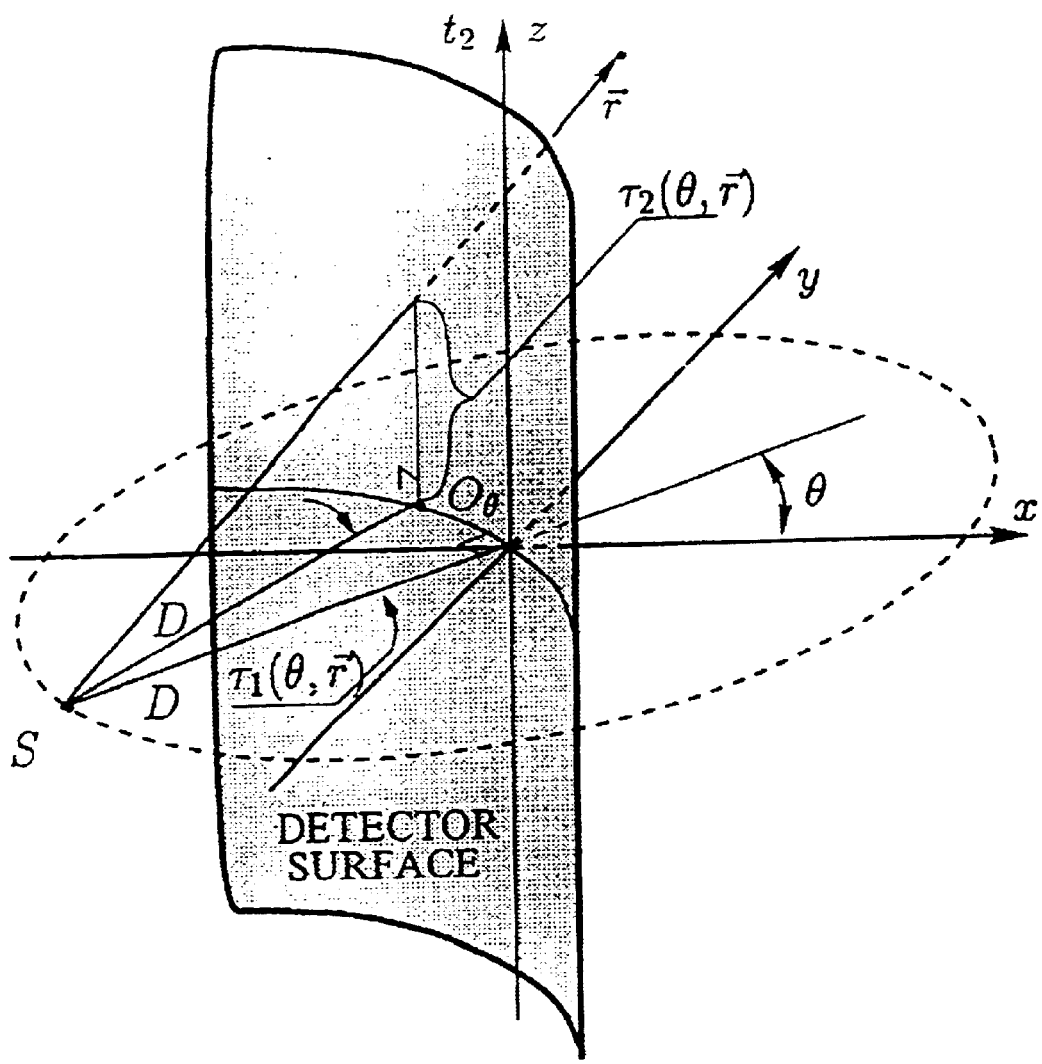
FIG. 6 is a diagram illustrating cone-beam tomography with a circular source orbit and a cylindrical detector.

Using the same definition for $K_M$ as in equation (8), the subimage backprojection operator $B_{M,P}[\vec{\delta}]$ is given by equation (9), where $\tau(\theta, \vec{r})$ is as defined earlier for the equiangular geometry (see FIG. 6). The part of g(p,•) that contributes to the backprojection onto f' is again $\hat{K}_M[\vec{\delta}]g$, where now $\hat{K}_M[\vec{\delta}]$ truncates g(p,•) in fan angle t to the angular support determined by the angles $t_A$ and $t_B$ of the projection of the support of the subimage $f'=K_M[\vec{\delta}]f$. The same discussion and arguments as in the colinear equispaced fan-beam geometry apply, leading to equations (10)–(12), and the exact decomposition illustrated in FIG. 9.

The approximate decomposition again reduces the number of projections used to reconstruct subimage f' using the following procedure. Let $t_{OO'}$ be the angle between the two rays passing through the centers O and O' of f and subimage f', respectively. In direct analogy to t-shifting the truncated projections by the interval $\overline{OO''}$ corresponding to the projection of the center O' of f' in the colinear equispaced detector case, the truncated projections for the subimage are t-shifted in fan angle by $t_{OO'}$. Evenly spaced sample points with the same angular spacing Δt are obtained centered on t=0. Thus, in the equiangular case the angular variable t takes the role of t appearing in the equispaced geometry, and $\tau(\theta, \vec{r})$ is defined as in FIG. 7. Otherwise, the same recursive decomposition process described before applies here. In particular, once tuncated fan-beam projections corresponding to a subimage have been shifted in t, they are decimated by L with respect to source angle θ, and the rest of the procedure is followed. The definitions of the various operators are little modified, except for the changes already listed. The approximate decomposition is again described by FIG. 11.

Similar arguments and modifications apply to the fast native reprojection algorithm.

Fast Native Backprojection and Reprojection Algorithms for Cone-beam Geometry with Planar Equispaced Detector The process for the general 3D divergent-beam geometry has the same components as described for the 2D case, with the following main differences:

1. The image is decomposed in 3D, along all three coordinates.
2. Because projections are two-dimensional, truncation, shifting and interpolation of individual projections are two-dimensional.
3. Projections are decimated (or interpolated) in source position θ along the orbit, rather than in source angle on the circle.
4. Because the source orbit is often not isotropic in 3D, the preferred decomposition may not be isotropic, and may be spatially varying.

Figure 23:
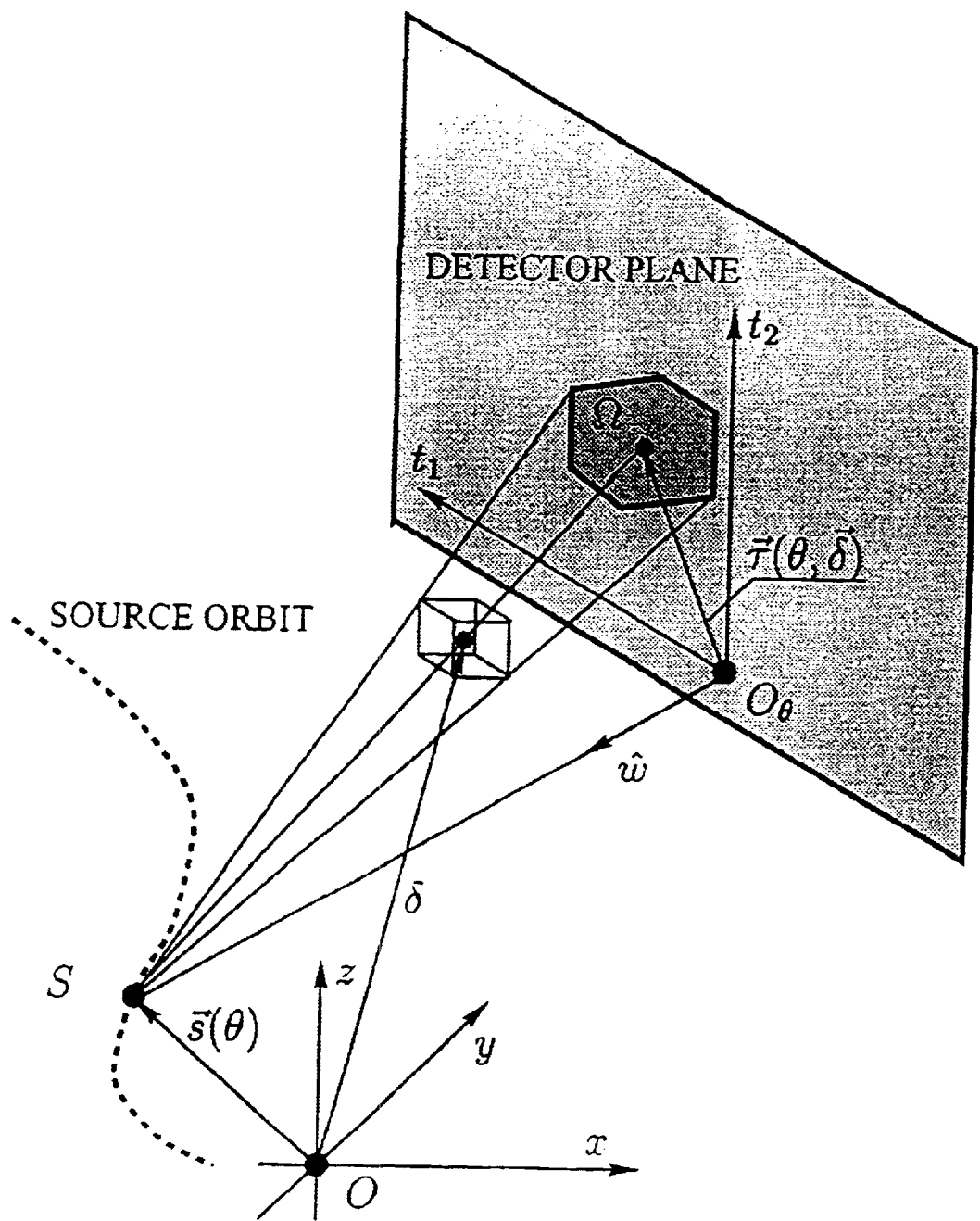
FIG. 23 is a diagram of a planar equispaced cone-beam projection geometry for a subimage.

Consider the backprojection operation for a sub-image f'($\vec{r}$) of f, shown in FIG. 23. Let $K_M[\vec{\delta}]$ be an image truncation operator defined by equation (8), so that $f'=K_M[\vec{\delta}]f$ is a sub-image of f, of size M×M×M centered at $O'=\vec{\delta}\epsilon_R^3$. Equations (9) and (10) still apply, with τ replaced by the 2D vector $\vec{\tau}$, and the truncation operator $\hat{K}_M[\vec{\delta}]$ truncating the projection of the entire object to the 2D support $\Omega$ of the projection of the M×M×M support of the subimage $f'=K_M[\vec{\delta}]f$ (see FIG. 23).

Figure 24:
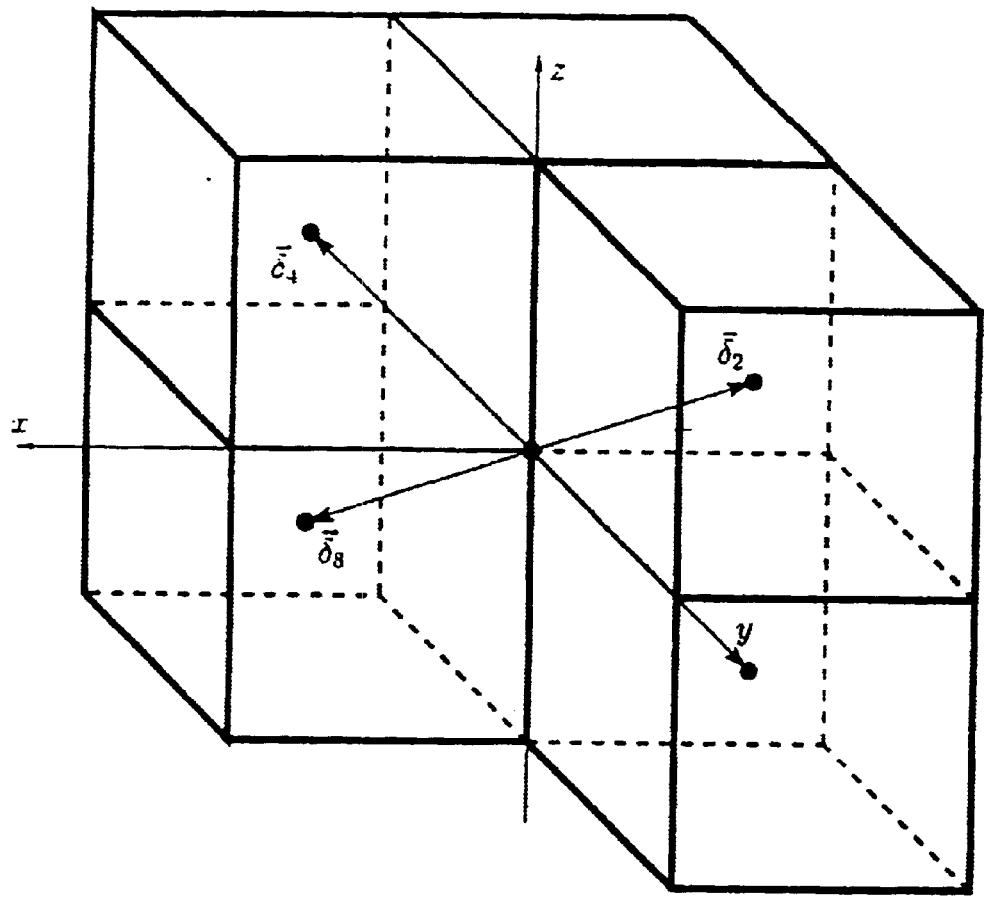
FIG. 24 is a diagram of a partition of a 3D image into subimages.

Consider now a partition of the image f into $J=(N/M)^3$ nonoverlapping subimages, each of size M×M×M, $$f = \sum_{j=1}^{J} \mathcal{K}_M[\vec{\delta}_j]f, \quad (24)$$

where vectors $\vec{\delta}_j, j=1,\ldots J$ are the centers of the subimages, as shown in FIG. 24 for the case M/N=2.

Equation (12) applies, providing an exact decomposition for the backprojection into backprojections onto the subimages. It is described by a figure analogous to FIG. 9, except that it would have eight instead of four "channels". The discussion of computational cost is similar to that in the 2D case, except that computational costs of $B_{N,P}$ and $B_{M,P}$ are $cN^3P$ and $cM^3P$, respectively, with a ratio J just as in the 2D case.

As in the 2D fan-beam case, the fast 3D cone-beam backprojection algorithm uses the decomposition idea with the following additional property. For fixed image resolution (bandwidth), the number of projections needed to reconstruct the image is proportional to the size of the image. That is, if P projections are needed to reconstruct an N×N×N image, then P'=(M/N)P projections suffice to reconstruct a M×M×M image to the same resolution.

Subimage $f'=K_M[\vec{\delta}]f$ is again reconstructed from a reduced number of projections, using operator $O[L,M,\vec{\delta}]$ to perform the reduction. It is defined by the composition of similar operators as before, with the following changes:

1. The projection truncation operator $K_M[\vec{\delta}]$ now truncates to the 2D region $\Omega$, as explained earlier.

2. The projection shift operators $\hat{M}_\pm[\vec{\delta}]$ perform a 2D shift by the vector $\pm \vec{r}(\theta,\vec{\delta})$ in the $t_1,t_2$ coordinates, instead of the 1D shift in the case of fan-beam geometry. This shift may be performed in a separable way, e.g., by first shifting in $t_1$, and then in $t_2$.

3. Operator $D_{\downarrow L}$ decimates in source position rather than in angle. When the orbit consists of the union of two or more distinct parts, such as two perpendicular circles, decimation in source position is performed separately for each part;

4. The filtering in the $\vec{t}$ variable involved in decimation per equation (14) is two dimensional rather than one dimensional. It too may be performed in separable form in $t_1$ and $t_2$, although the $\vec{t}$ filtering may or may not be separable from the filtering in $\theta$.

The approximate decomposition is again given by equation (18), where now $B_{M,P/L}$ is a divergent-beam backprojection in the global coordinate system onto an M×M×M subimage using P/L projections as defined by equation (9). For L=N/M=2 this decomposition is described by a figure analogous to FIG. 10, except that it would have eight instead of four "channels". The discussion of computational cost is similar to that in the 2D case, except that the computational costs of $B_{N,P}$ and $B_{M,P/L}$ are $cN^3P$ and $cM^3P/L$, respectively, and $J=(N/M)^3$. The total cost of J subimage backprojections is again L times smaller than that for the conventional whole-image backprojection $B_{N,P}$.

In a preferred embodiment of the fast backprojection algorithm, the decompositions of equations (12) and (18) are applied recursively, at each level further partitioning the subimages into smaller subimages in accordance with equation (24). The description of the process and various features and improvements presented earlier for the fan-beam geometry apply to the general cone-beam geometry as well, with changes similar to those listed for the exact and approximate decompositions themselves. In particular, the total cost of cone-beam backprojection using the recursive decomposition algorithm becomes $O(N^3 \log N)$, as compared to $O(N^4)$ for conventional cone-beam backprojection.

To this point, we have described the simplest embodiment of a 3D image decomposition, in which the image is equally decomposed in all three axes. However, in some instances of cone-beam geometry, because the source orbit is not isotropic in 3D, the preferred decomposition may not be isotropic either, and furthermore may be spatially varying. Important examples are the single-circle and helical cone-beam orbits (FIGS. 4, 6, and 3). These cases exhibit cylindrical symmetry (or near symmetry) of the source orbit around the z-axis, and the image partition chosen in the z axis may be different from that in the x and y axes. Even when the entire orbit does not have a symmetry axis, it may be sometimes decomposed into the union of parts that do, as in the case of a source orbit consisting of two perpendicular circles. The backprojection operation can then be performed as the sum of two backprojections, each with its own separate axially symmetric orbit.

Figure 25:
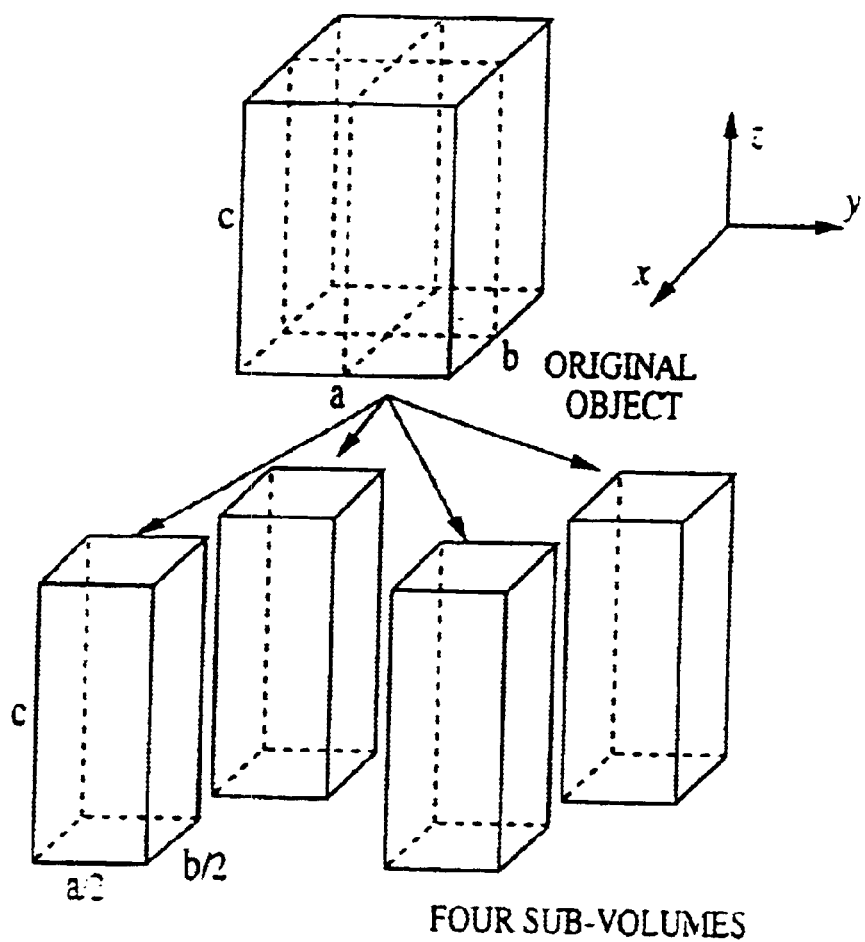
FIG. 25 is a diagram of a nonisotropic partition of a 3D image into subimages.
Figure 26:
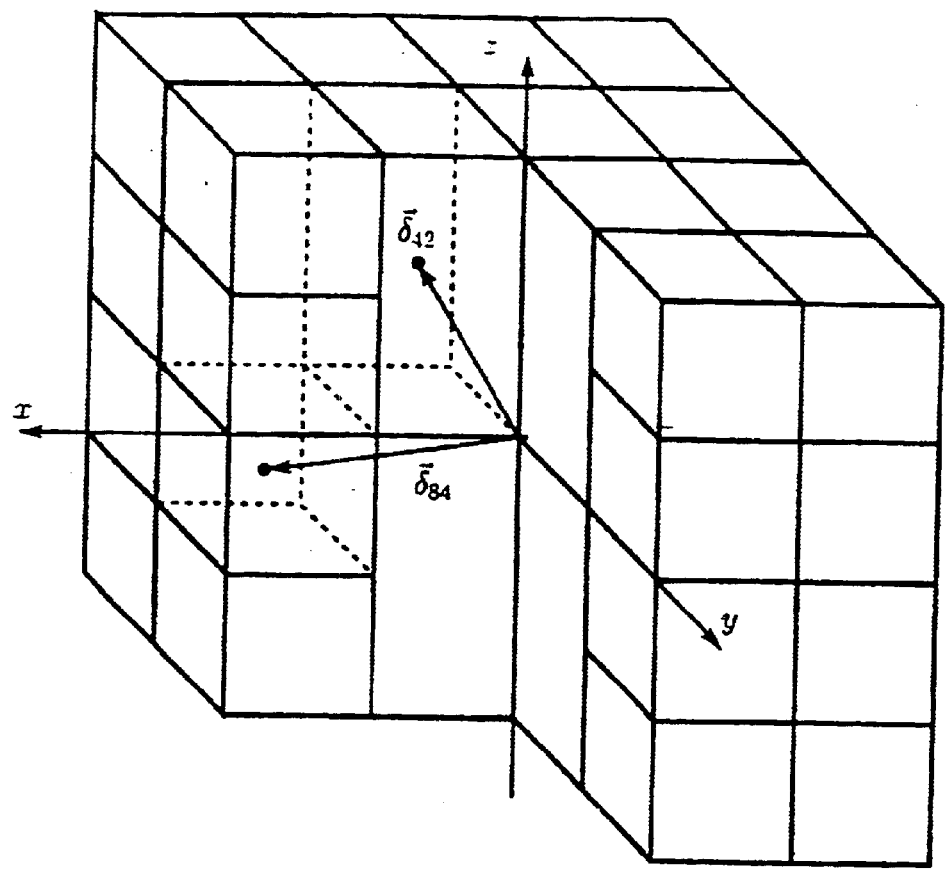
FIG. 26 is a diagram of a two-level nonuniform recursive partition of a 3D image.
Figure 27A:
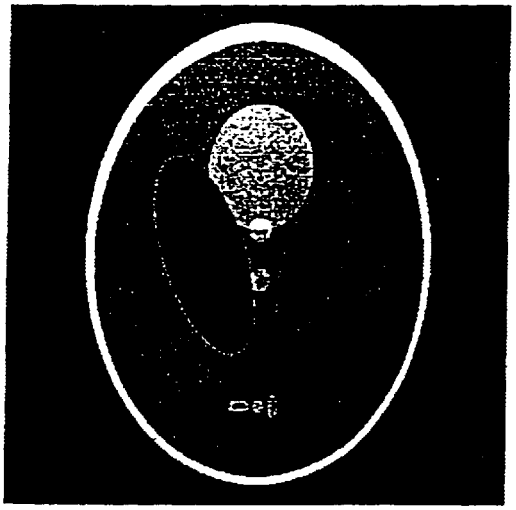
FIGS. 27(a)–27(d) are pictures comparing exact and fast fan-beam backprojections for collinear equispaced detectors.
Figure 27B:
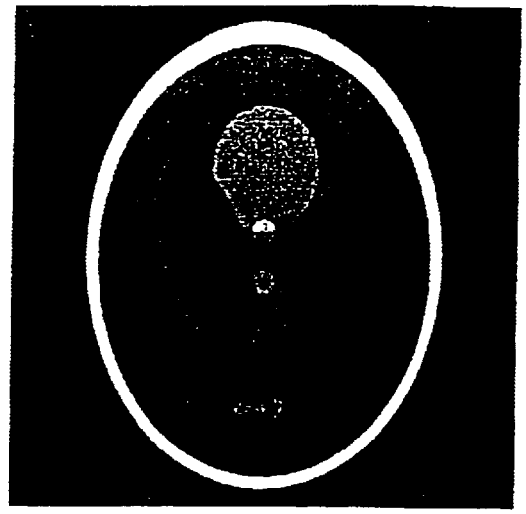
Figure 27C:
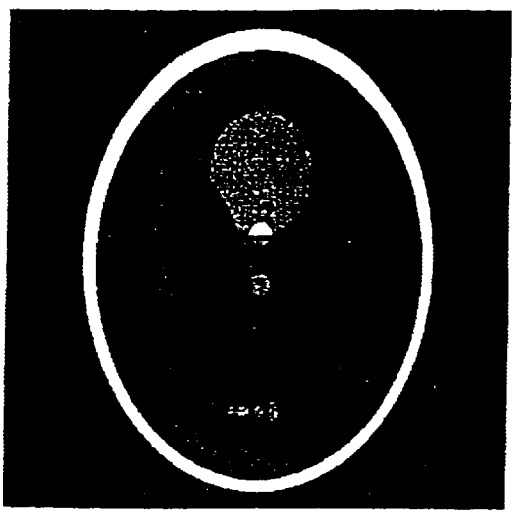
Figure 27D:
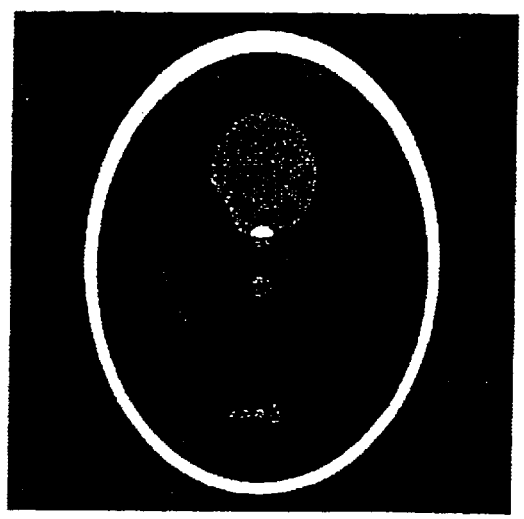
Figure 28A:
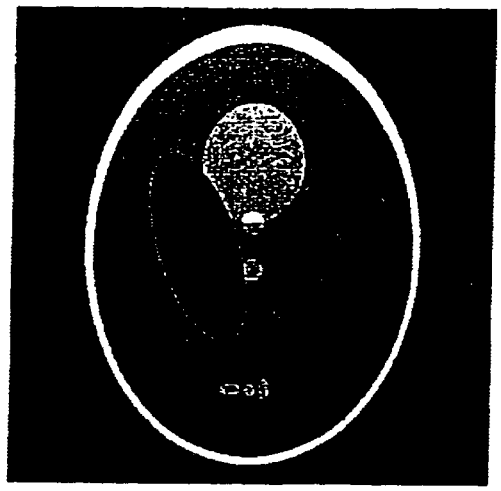
FIGS. 28(a)–28(d) are pictures comparing exact and fast fan-beam backprojections for equiangular detectors.
Figure 28B:
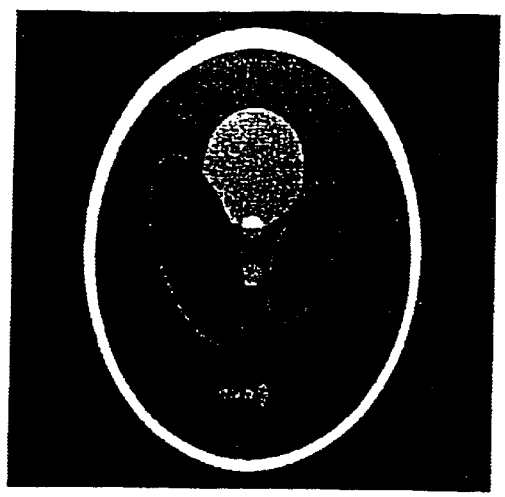
Figure 28C:
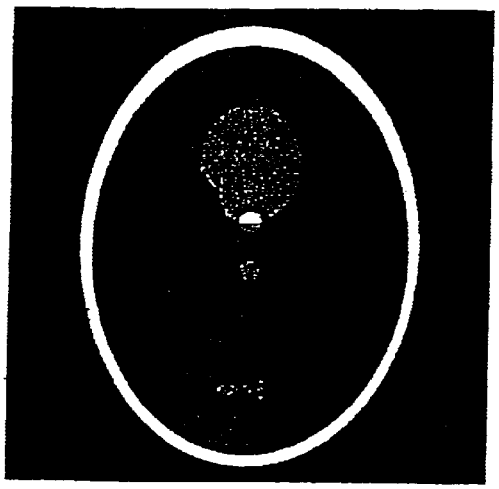
Figure 28D:
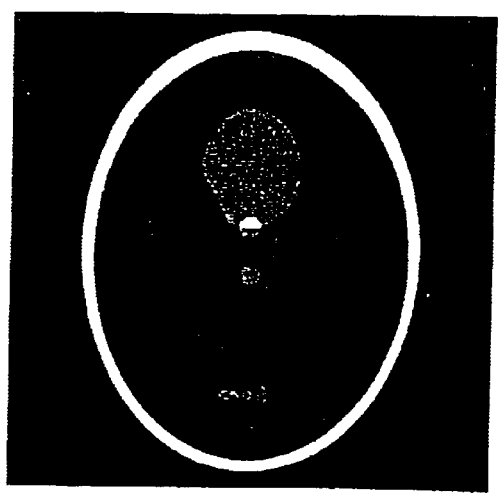

In such instances, it may be sufficient to partition parts of the image less frequently, or into subimages of larger size in the z axis. In an extreme example, the partition may be restricted altogether to the (x,y) directions, as shown in FIG. 25. A more general nonisotropic and spatially nonuniform partition is shown in FIG. 26. This can lead to computational savings, by reducing the number of required shifts, interpolations, or filtering operations on projections along the $t_2$ axis.

The reason such reduced partitioning works, is seen by examining equations (2) and (3) in the case of a single circular source orbit. The equations describe the $\theta$ dependence of the position of the projection of a point onto the detector. Consider a point $\vec{r}$ with small z and/or small $\sqrt{x^2+y^2}$. That is, a point close to the plane of the source orbit, and/or near the z axis. Note that for such a point, $\tau_2(\theta,\vec{r})$ will vary much slower with $\theta$ than will $\tau_1(\theta,\vec{r})$. This can be used to show that a subimage whose center $\vec{\delta}$ is so located can be accurately reconstructed from a reduced number of views even if its z-dimension is not reduced by the same proportion as its (x,y) dimensions. As a result, the finer partitioning in the (x,y) plane is sufficient to ensure accurate reconstruction from a reduced number of projections. A similar argument applies in the case of a helical orbit, if a global shift by $h\theta/(2\pi)$ in $t_2$ is first applied to the projections to compensate for the motion of the center of coordinates on the detector along the z axis, with varying $\theta$ (see FIG. 3).

With such nonisotropic and possibly nonuniform partitioning, the recursive decomposition is modified accordingly. If the partition of FIG. 25 is used recursively, the corresponding decomposition will have four channels at each level of the recursion, involving shifts only in the $t_1$ variable, and will be described by FIGS. 10–15. On the other hand, if the partition of FIG. 26 is used in a two-level approximate decomposition, the first level of the decomposition will have eight channels (corresponding to the eight octants of the coarse partition of the cube), but then each of the decompositions in the next level will only have seven channels corresponding to the seven images into which each coarse image octant is partitioned.

The design of a fast reprojection for the general divergent-beam geometry, including the specific instances of divergent-beam geometry discussed earlier, is the dual of the corresponding fast backprojection algorithms. It bears the same relationship to fast divergent-beam geometry backprojection as fast fan-beam reprojection bears to fast fan-beam backprojection. Because the latter relationship has been described in some detail already, we do not repeat it here.

Implementations and Experiments

The new algorithms have been implemented in MATLAB™ and C programming languages, and successfully tested in several numerical experiments involving the reconstruction of the Shepp-Logan head phantom (a standard test image used in numerical evaluations of tomographic algorithms) of size N×N=512×512 in the 2D case, and of size N×N×N=128×128×128 in the 3D case. We used the so-called unmodified phantom, with a realistic (and high) contrast between the skull and brain. This presents a challenging test for the algorithms, because even slight artifacts created by the reconstruction of the skull are prominent on the brain background.

We first describe the results of 2D fan-beam reconstruction. For both equispaced and equiangular fan-beam imaging geometries we set the source-to-image-center distance to 1.25 times the image size, i.e., D=1.25N, and the total fan angle to $2\alpha_0=1.17$ radians, with 1025 detectors on the fan. We generated full-scan fan-beam projection data with P=1536 evenly spaced source angles, $\theta_p \in [0,2\pi)$ for the 10-ellipse phantom, using analytical expressions for the line integrals through an ellipse.

In our simulations, at each level we decomposed the image into 4 subimages of half the size. For the approximate decompositions we used a decimation factor L=2. The image was decomposed iteratively to single pixel subimages, i.e., $M_{min}=1$. To increase the angular oversampling, the first Q levels of the decomposition were exact decompositions, without angular decimation. We used Q=2 and Q=3, where Q is referred to as the "holdoff parameter". The parameters ("footprint") for the projection truncation operator $\hat{K}_K[\vec{\delta}]$ were computed on-the-fly using a simple conservative approximation, at the cost of some increase in computation.

Figure 29A:
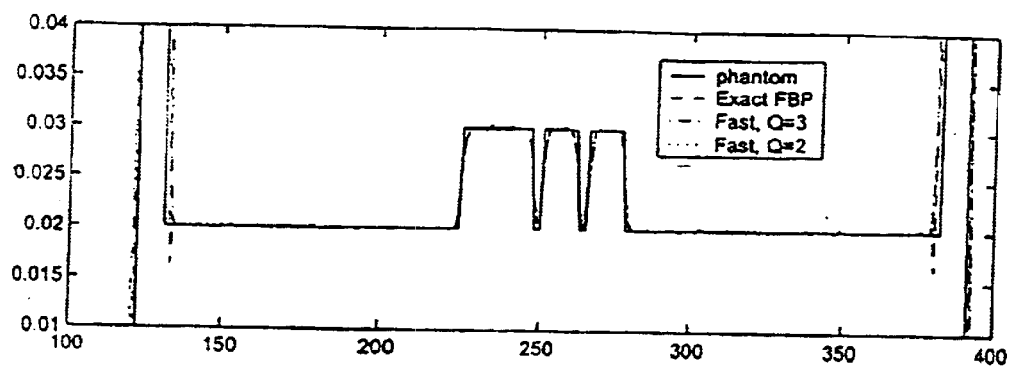
FIGS. 29(a) and 29(b) are plots taken through slices of the backprojections of FIGS. 28(a)–28(d)
Figure 29B:
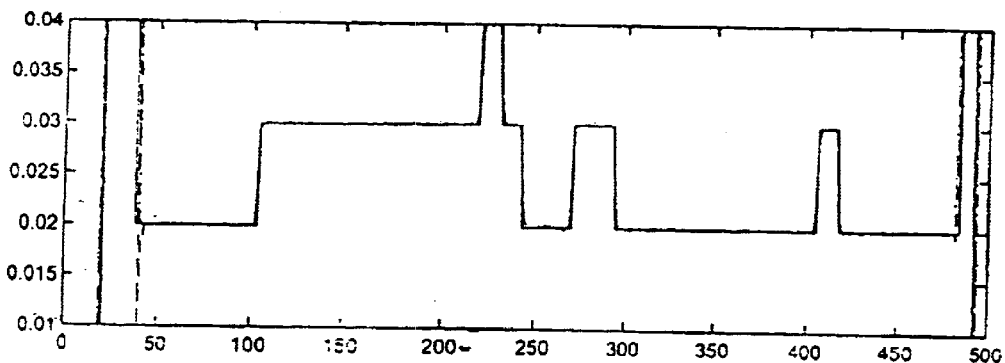

FIGS. 27 and 28 compare the exact backprojection algorithm and our fast fan-beam backprojection algorithms for the two fan-beam imaging geometries. As a reference and benchmark, FIGS. 27(a) and 28(a) show the original phantom, and FIGS. 27(b) and 28(b) are the reconstructed images using exact fan-beam backprojection for both equispaced and equiangular detectors. FIGS. 27(c), 28(c), 27(d) and 28(d) are the reconstructions using our fast algorithms with holdoff parameter Q=3 and Q=2, respectively. The speedups of the fast algorithms are 30× and 60× for holdoff Q=3 and Q=2, respectively. The reconstructions using the exact and fast algorithms show little if any perceptual quality difference, even for Q=2. Plots through rows and columns of the reconstructed images in FIG. 28 are shown in FIGS. 29(a) and 29(b). FIG. 29(a) compares slices through the $410^{th}$ row, and FIG. 29(b) compares slices through the $356^{th}$ column from FIG. 28. In these plots, the solid line represents the original phantom, the dashed line represents the exact fan-beam backprojection, the dashed-dotted line represents the fast algorithm with holdoff 3, and the dotted line represents the fast algorithm with holdoff 2.

Next, we compare the point-spread functions (PSF's) of the exact and fast fan-beam backprojections algorithms for the equispaced detector geometry. We ran the exact and fast algorithms on an image of size 256×256 with four point targets located at positions (10,10), (128,128), (49,37), and (201,93). We used parameters similar to those used before: source to center distance D=1.25N, number of source angles P=2N, and total fan angle of 1.20 radians with 737 equispaced detectors. The point responses were very similar at all four positions, suggesting essentially shift-invariant response. The point spread functions (PSF's) for the point target at (128,128) obtained with the exact and fast algorithms (with Q=3) are compared in FIGS. 30(a) and 30(b).

Figure 30A:
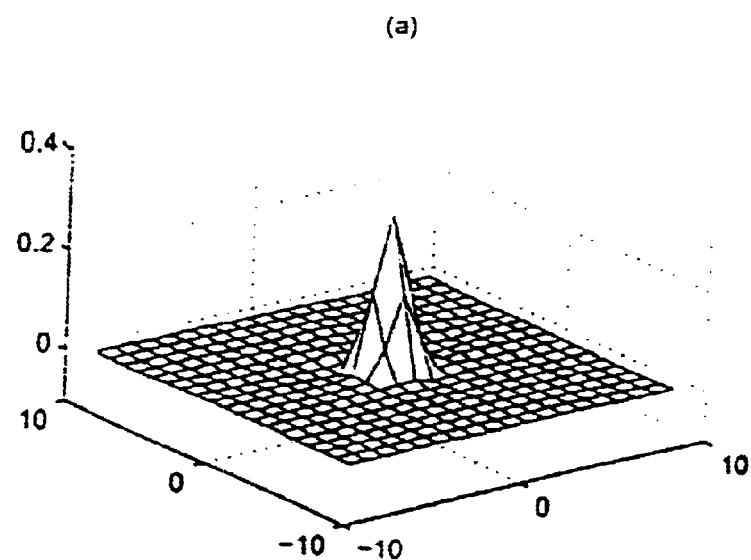
FIGS. 30(a) and 30(b) are comparisons of point spread functions.
Figure 30B:
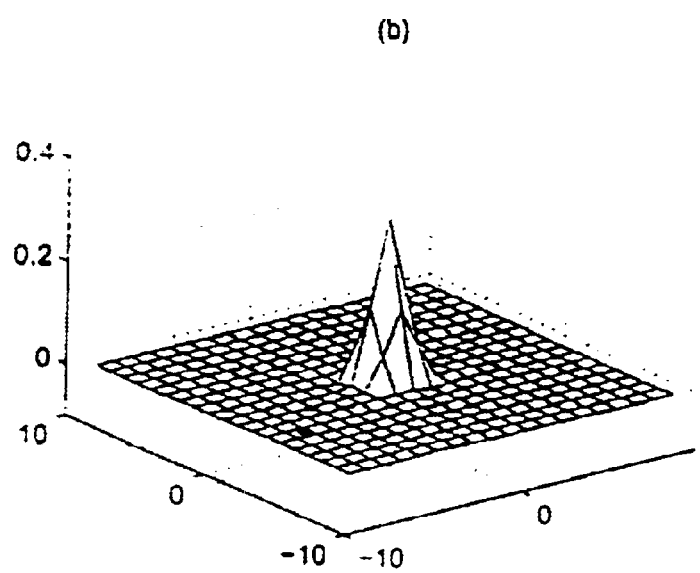
Figure 31A:
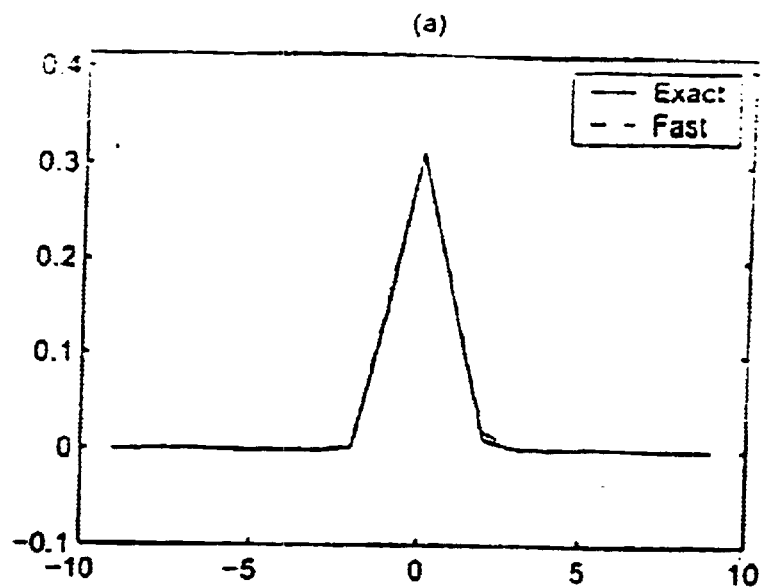
FIGS. 31(a) and 31(b) are comparisons of plots of slices through point spread functions.
Figure 31B:
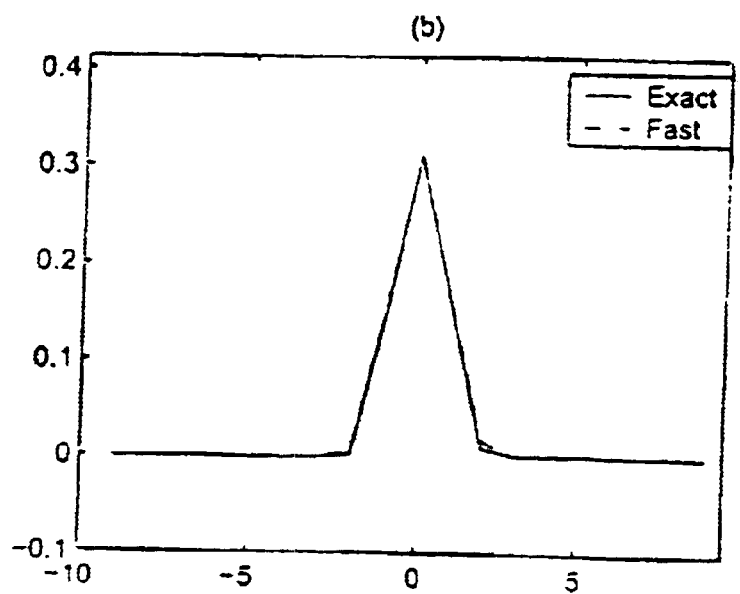

FIG. 30(a) illustrates a center pixel PSF for the exact algorithm, and FIG. 30(b) illustrates a center pixel PSF for the fast algorithm with holdoff equals 2. Slices through the two axes of the PSF's are shown in FIGS. 31(a) and 31(b). FIG. 31(a) represents a slice through the $128^{th}$ row for the exact algorithm (solid line) and the fast algorithm with Q=3 (dashed line). FIG. 31(b) represents a slice through the $128^{th}$ column for the exact algorithm (solid line) and the fast algorithm with Q=3 (dashed line). The PSF's of the two algorithms are almost identical, confirming the accuracy of the fast algorithms.

Next, we discuss the results of experiments with cone-beam reconstruction with a single circular source orbit in the (x,y) plane. The distance from the source to the center of the volume was 1.25 times the length of the lateral. Cone-beam projections were taken at 512 source angles, which were uniformly spaced in $[0,2\pi)$. The fan angle (in azimuth) was 1.20 radians, and the cone angle was 1.5 radians. We considered both the planar equispaced and cylindrical detector geometries shown in FIG. 4 and FIG. 6, respectively. In each case, the detector surface consisted of 375×375 detectors equispaced along the vertical ($t_2$) axis, and at either equispaced or equiangular intervals in the $t_1$ coordinate.

The conventional reconstruction algorithm for the single circle cone-beam orbit with a planar detector is the well-known Feldkamp, Davis and Kress (FDK) algorithm, which consists of weighting the projections, filtering along the $t_1$ coordinate, and then performing weighted cone-beam backprojection. The weighting and filtering are the same as for the fan-beam geometry with a planar detector, the difference being in the use of cone-beam rather than fan-beam backprojection. This is an approximate algorithm, and it suffers from some inherent artifacts at large cone angles. Nonetheless, it is a standard benchmark for this cone-beam geometry. For the cylindrical detector geometry we used the analogous algorithm, obtained by extending the fan-beam algorithm for the equiangular detector geometry to the cone-beam geometry by incorporating a weighted cone-beam backprojection onto the cylindrical detector.

For demonstration purposes, the corresponding fast algorithms used backprojection with the recursive decompositions described earlier, with the simple partitioning scheme shown in FIG. 25. In our simulations, we terminated the decomposition process when the subimage size was reduced to 4×4×128, since the overhead involved in our particular implementation of the algorithm offset the speedup of the backprojection operators for such small volumes. The fast algorithms used the same filtering and weighting as the conventional FDK algorithm.

Figure 32:
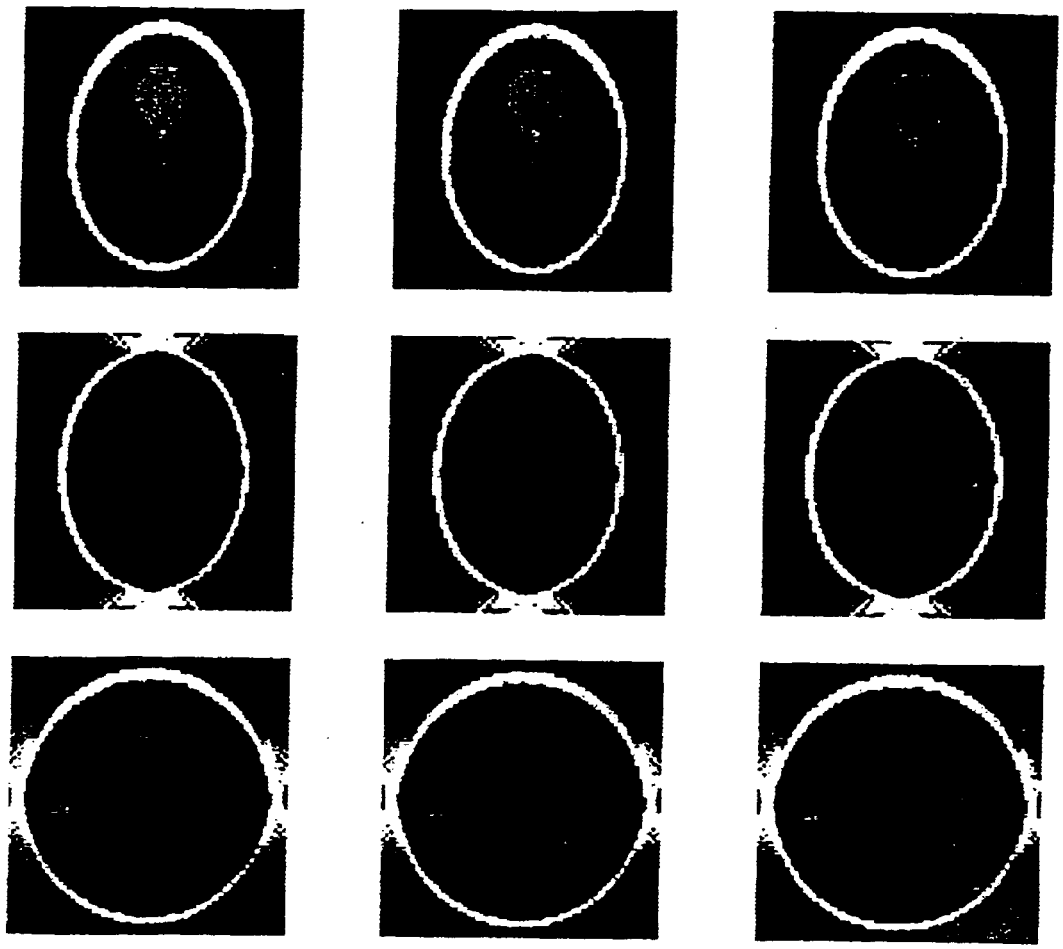
FIG. 32 is a collection of pictures of 3D cone-beam reconstructions.
Figure 33:
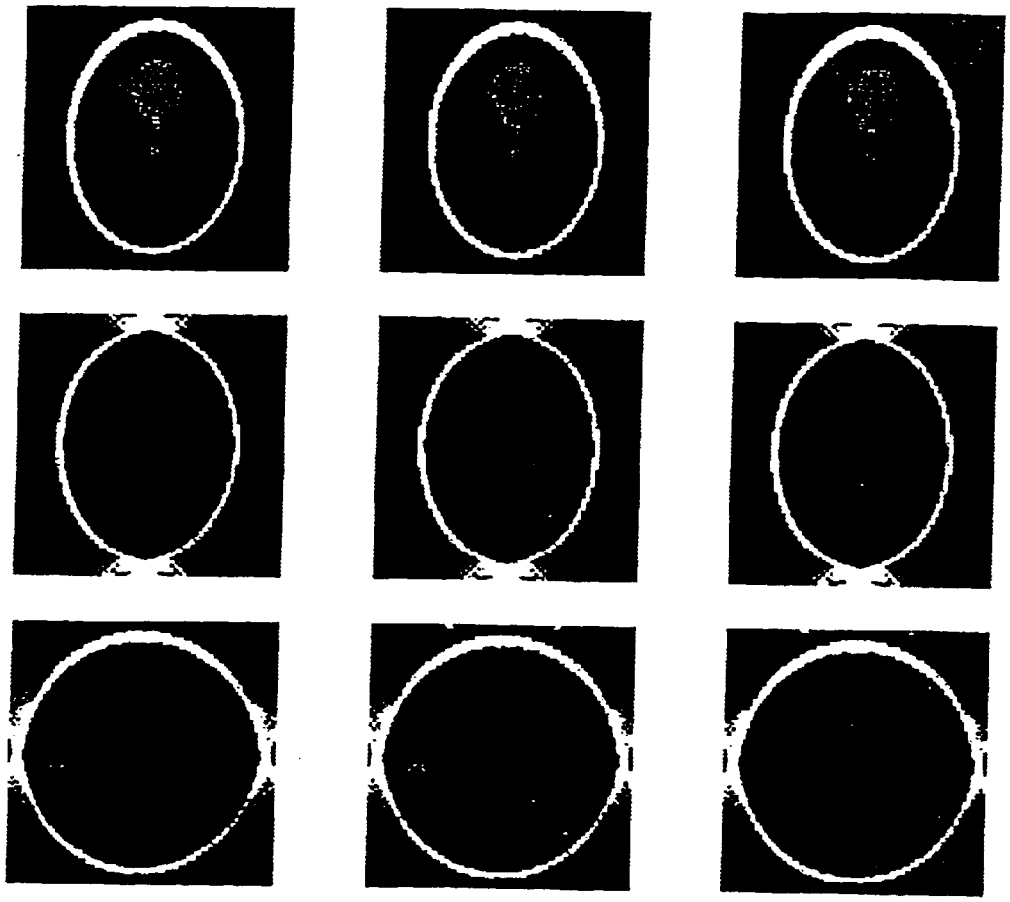
FIG. 33 is another collection of pictures of 3D cone-beam reconstructions.
Figure 34:
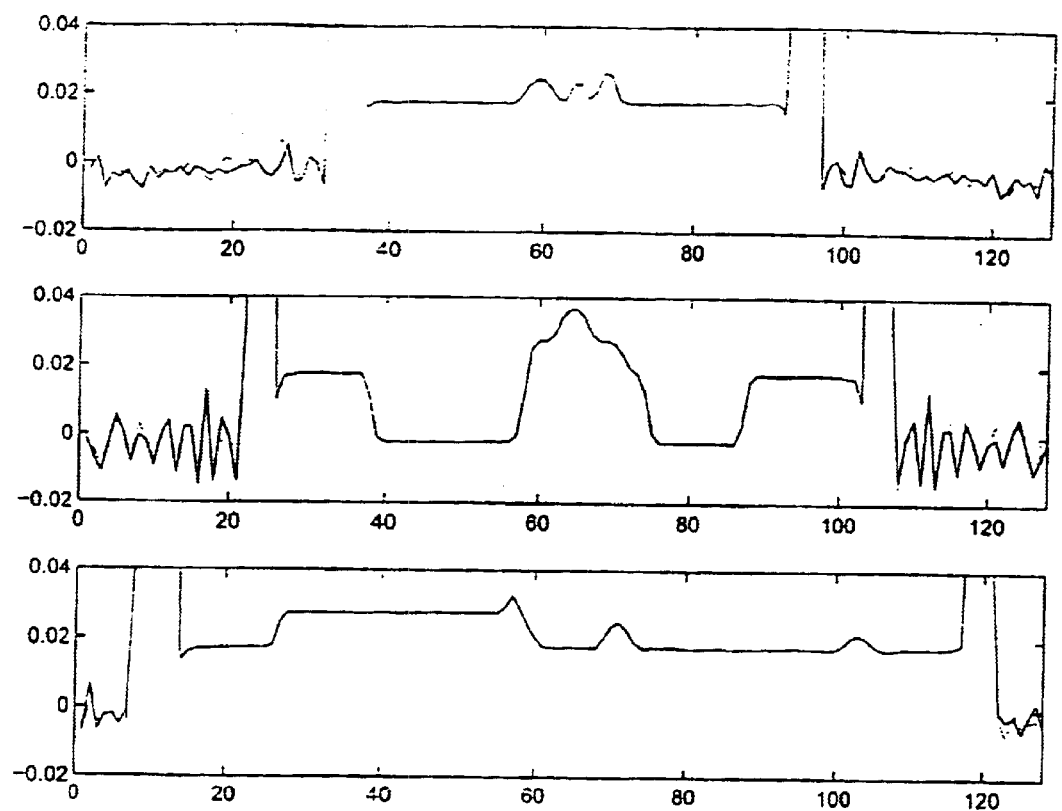
FIG. 34 is a collection of plots of slices through images in FIG. 32.
Figure 35:
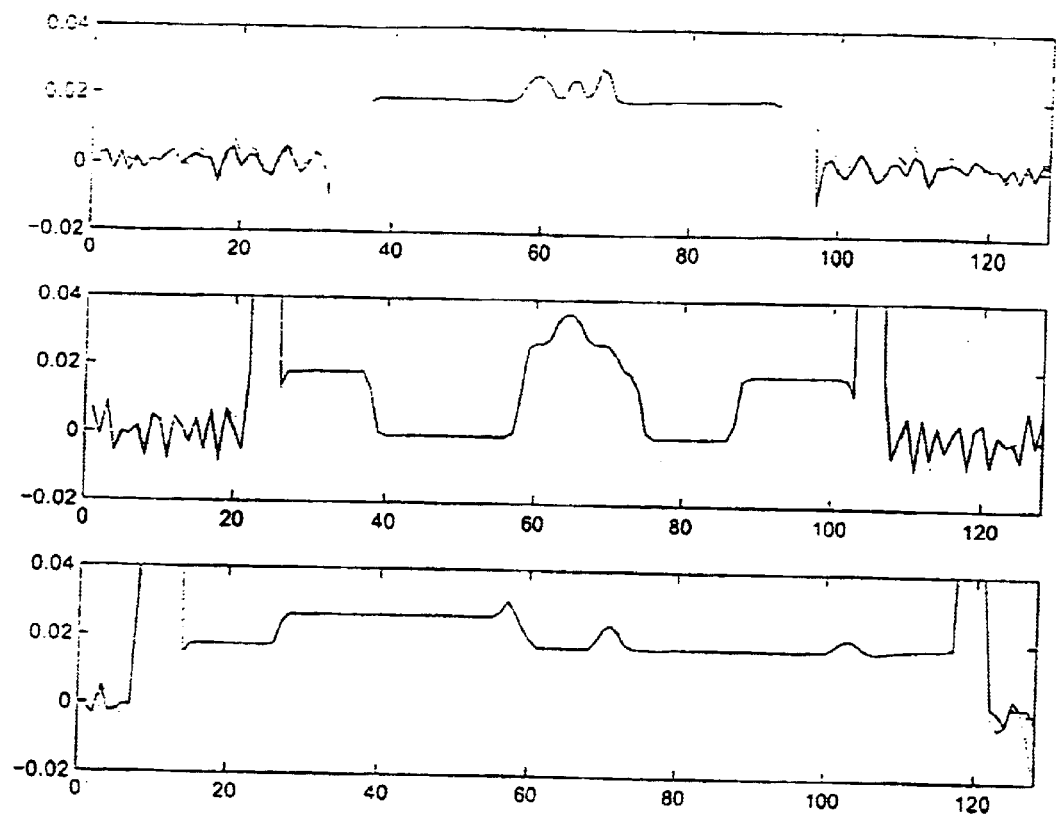
FIG. 35 is a collection of plots of slices through images in FIG. 33.

The results of conventional FDK reconstruction and fast reconstruction using the process of this invention are compared in FIG. 32 and FIG. 33 for the planar and cylindrical detector geometries, respectively. FIG. 32 compares 3D conebeam reconstructions for a singular circular orbit and a planar equispaced detector geometry. The top row is an xy slice at z=−0.25, the middle row is a yz slice at x=−0.13, and the bottom row is an xz slice at y=−0.04. The left column is the reconstruction result using the conventional FDK algorithm, and the middle and the right columns use the fast algorithm of the present invention, with holdoff 2 and 1, respectively. FIG. 33 is a comparison of 3D conebeam reconstructions for a singular source orbit and a cylindrical detector geometry. The top row is an xy slice at z=−0.25, the middle row is a yz slice at x=−0.13, and the bottom row is an xz slice at y=−0.04. The left column is the reconstruction result using the conventional FDK algorithm, the middle and right columns use the fast algorithm of the present invention with holdoff 2 and 1, respectively. FIG. 34 represents slices through images in the corresponding rows in FIG. 32. The top plot illustrates row 102, the middle plot illustrate row 80 and the bottom plot illustrates column 81. The solid lines are from the conventional FDK reconstruction. The fast algorithm with holdoff 2 is shown in dashed-dotted lines, and the fast algorithm with holdoff 1 is shown in dotted lines. FIG. 35 illustrates slices through images in the corresponding rows in FIG. 33. The top plot illustrates row 102, the middle plot illustrates row 80 and the bottom plot illustrates column 81. The solid lines are from the conventional FDK reconstruction, the dashed-dotted lines represent results using the fast algorithm with holdoff 2 and the dotted lines represent results using the fast algorithm with holdoff 1. Additional detail is provided by FIGS. 34 and 35, which show plots of the reconstructed density along certain lines through the images of FIGS. 32 and 33. Results for both holdoff=1, and holdoff=2 are given.

The fast version of the FDK algorithm using the present invention with holdoff factor Q=2 is about three times faster then the conventional Feldkamp algorithm, with little if any degradation in image quality. Even with holdoff factor Q=1, the image quality is acceptable for some applications, with a 7-fold speedup. We expect the speedup will increase to tens for 512×512×512 image volumes and full-fledged 3D partitioning as in FIG. 24 or 26 and corresponding decomposition. (In fact, in cone-beam geometries with near cylindrical symmetry, such as circular or helical orbit, speedups of tens will be obtained for 512×512×H images for any z-size H).

Experimental Conclusion

In our experiments in 2D, the new fan-beam backprojection algorithms provided practical speedups of 30×–60× for 512×512 images with no perceivable loss in accuracy. In 3D, with the single circle orbit and planar detector cone-beam geometry, and using the simplest form of the decomposition, the speedup was 3×–7× for 128×128×128. Speedup factors in the tens should be possible with a full-fledged implementation of the proposed decomposition of this invention, and for 512×512×512 images.

The experiments demonstrated the effectiveness of the process of this invention for different detector geometries. These results for the simple single circular orbit geometry will extend to the more general divergent-beam geometry, such as helical conebeam. Because of the similarity in principles and structure between the reprojection and backprojection algorithms, similar results should hold for the fast divergent-beam reprojection algorithms of this invention. Both reprojection and backprojection algorithms are useful individually; in combination, they can be used for various iterative approaches to tomographic reconstruction, or for artifact correction in tomography, as explained, for example, in U.S. Pat. Nos. 6,263,096 and 6,351,548. A combination of backprojection and reprojection can also be used to construct fast reconstruction algorithms for the long object problem in the helical cone-beam geometry.

While the principles of the invention have been described above in connection with specific apparatus and applications, it is to be understood that this description is made only by way of example and not as a limitation on the scope of the invention.

What is claimed is:

1. A method for generating an electronic image from a divergent-beam sinogram which is amenable to backprojection, comprising the steps of:
   subdividing the sinogram into a plurality of sub-sinograms;
   performing a weighted backprojection of said sub-sinograms in the global coordinate system to produce a plurality of corresponding sub-images at proper locations in the global coordinate system; and
   aggregating said sub-images to create the electronic image.

2. The method of claim 1 wherein said sinogram subdivision is approximate.

3. The method of claim 1 wherein said sinogram is subdivided into a plurality of sub-sinograms in a recursive manner until each sub-sinogram represents a sub-image of a desired size, where said subdividing steps include a desired number of exact subdivisions and a desired number of approximate subdivisions.

4. The method of claim 3 wherein said exact subdivision steps include truncation without shifting.

5. The method of claim 3 wherein said sub-sinograms correspond to sub-images as small as one pixel or voxel in size.

6. The method of claim 1 wherein said aggregation step is performed in a recursive manner.

7. The method of claim 1 wherein said electronic image is a tomographic image.

8. The method of claim 1 further comprising preprocessing in which oversampling in the data coordinates is used to improve the accuracy of the electronic image.

9. The method of claim 1 wherein the sinogram includes preprocessed divergent-beam projections.

10. The method of claim 1 wherein said sinogram subdivision steps are approximate, and include truncation, shifting, and decimation of the sinogram, so that each sub-sinogram produced corresponds to a subimage in the global coordinate system.

11. The method of claim 10 wherein said approximate subdivision steps also include weighting.

12. The method of claim 10 wherein said subdivisions are performed recursively, and wherein said shifting operations in successive stages of the recursion are combined to reduce computational cost.

13. The method of claim 1 wherein subdivisions are performed non-isotropically and nonuniformly in space, so that sub-images in a given level of recursion need not be of the same shape or size.

14. The method of claim 13 wherein the partition is chosen in accordance with the symmetry properties of the source orbit, to achieve a desired tradeoff between computational cost and image accuracy.

15. The method of claim 1 wherein the method is applied individually to multiple sinograms, acquired from multiple source orbits, to produce images that may be combined to produce a final image.

16. The method of claim 1 wherein the exact subdivision step is arranged such that the operation of truncation of projections in a sinogram or sub-sinogram for a subimage begin after one or more projections become available for this subimage.

17. The method of claim 1 wherein the subdivision step is arranged such that the subdivision of a sinogram for a subimage begins after one or more projections become available for this subimage.

18. The method of claim 1, applied sequentially in time to multiple divergent-beam sinograms as they become available.

19. The method of claim 1 wherein the divergent-beam sinogram is acquired within a convergent-beam geometry.

20. Apparatus for generating an electronic image of an object comprising:
   means for scanning the object to generate data representing an image of the object;
   means for manipulating said data to generate a processed sinogram;
   means for subdividing said sinogram into a plurality of sub-sinograms;
   means for backprojecting each of said sub-sinograms in the global coordinate system to produce a plurality of corresponding sub-images at proper locations in the global coordinate system;
   means for aggregating said sub-images to create the electronic image; and
   means for storing, and/or displaying, and/or analyzing the electronic image.

21. The apparatus of claim 20 wherein said sinogram subdivision is approximate.

22. The apparatus of claim 20 wherein said sinograms are subdivided into a plurality of sub-sinograms in a recursive manner until each sub-sinogram corresponds to a subimage of a desired size, and said means for subdividing performs a desired number of exact subdivisions and a desired number of approximate subdivisions.

23. The apparatus of claim 22 wherein said exact subdivisions include truncation without shifting.

24. The apparatus of claim 22 wherein said sub-sinograms correspond to images a small as one pixel or one voxel in size.

25. The apparatus of claim 20 wherein said means for aggregating operates in a recursive manner.

26. The apparatus of claim 20 wherein said electronic image is a tomographic image.

27. The apparatus of claim 20 wherein said means for processing performs oversampling in the data coordinates to improve the accuracy of the electronic image.

28. The apparatus of claim 20 wherein said sinogram subdivision steps are approximate, and include truncation, shifting, and decimation of the sinogram, so that each sub-sinogram produced corresponds to a sub-image in the global coordinate system.

29. The apparatus of claim 28 wherein the approximate subdivision steps may also include weighting.

30. A method for generating a divergent-beam sinogram from an electronic image, comprising the steps of:
   dividing the image into a plurality of sub-images;
   computing sub-sinograms of each said sub-image in the global coordinate system; and
   aggregating said sub-sinograms to create the sinogram;
   wherein said computation of at least one of said sub-sinograms is approximate.

31. The method of claim 30 wherein said subdivision is performed in a recursive manner until each said sub-image has a desired size, and said computation of sub-sinograms is approximate in a desired number of levels in the recursion, and exact in the remaining levels of the recursion.

32. The process of claim 30 wherein said aggregations are performed in a recursive manner.

33. The process of claim 31 wherein said exact computation of sub-sinograms is performed without shifting.

34. The process of claim 33, wherein said aggregations are preformed in a recursive manner.

35. The process of claim 33, wherein said approximate computation of sub-sinograms is performed by shifting, interpolating, and adding sub-sinograms, and each shifted and interpolated sub-sinogram corresponds to a sub-image in the global coordinate system.

36. The process of claim 35, wherein said steps of approximate computation of sub-sinograms also include weighting.

37. The process of claim 30 wherein said approximate computation of sub-sinograms is performed by shifting, interpolating, and adding sub-sinograms, and each shifted and interpolated sub-sinogram corresponds to a sub-image in the global coordinate system.

38. The process of claim 37, wherein said steps of approximate computation of sub-sinograms also include weighting.

39. Apparatus for creating an image of an object, comprising:
   a scanner which generates data from the object;
   a processor for creating at least one divergent-beam projection of the image;
   means for reconstructing, or in the case of iterative reconstruction apparatus, backprojecting an image from at least one projection;
   means for detecting errors in the image produced by the reconstruction means;
   means for reprojecting an image after error correction, performing additional corrections to the sinogram, and feeding the corrected sinogram to said reconstruction or backprojection means; and
   means for displaying the image created by the reconstruction means after the errors are corrected,
   wherein said reprojecting means divides the image into a plurality of sub-images, computes sub-sinograms of said sub-images in the global coordinate system, and aggregates said sub-sinograms to create the image sinogram;
   wherein said aggregations are performed by adding sub-sinograms, without shifting.

40. The apparatus of claim 39 wherein said computation of at least one sub-sinogram is approximate.

41. The apparatus of claim 39 wherein said subdivision is performed in a recursive manner until each said sub-image has a desired size, and said computation of sub-sinograms is approximate in a desired number of levels in the recursion, and exact in the remaining levels of the recursion.

42. The apparatus of claim 39 wherein said aggregations are performed in a recursive manner.

43. The apparatus of claim 40 wherein said approximate computation of sub-sinograms is performed by shifting, interpolating, and adding sub-sinograms, and each shifted and interpolated sub-sinogram corresponds to a sub-image in the global coordinate system.

44. The apparatus of claim 43, wherein said approximate computation of sub-sinograms also includes weighting.

* * * * *